US010335608B2

(12) United States Patent
Mandel et al.

(10) Patent No.: US 10,335,608 B2
(45) Date of Patent: Jul. 2, 2019

(54) PHOTODYNAMIC COMPOUNDS AND METHODS FOR ACTIVATING THEM USING IONIZING RADIATION AND/OR OTHER ELECTROMAGNETIC RADIATION FOR THERAPY AND/OR DIAGNOSTICS

(71) Applicants: THERALASE TECHNOLOGIES, INC., Toronto (CA); UNIVERSITY HEALTH NETWORK, Toronto (CA)

(72) Inventors: Arkady Mandel, Toronto (CA); Carl Fisher, Mississauga (CA); Lothar Lilge, Toronto (CA)

(73) Assignees: THERALASE TECHNOLOGIES, INC., Toronto (CA); UNIVERSITY HEALTH NETWORK, Toronto (CA)

( * ) Notice: Subject to any disclaimer, the term of this patent is extended or adjusted under 35 U.S.C. 154(b) by 0 days.

(21) Appl. No.: 15/492,801

(22) Filed: Apr. 20, 2017

(65) Prior Publication Data

US 2017/0304648 A1 Oct. 26, 2017

Related U.S. Application Data

(60) Provisional application No. 62/325,226, filed on Apr. 20, 2016.

(51) Int. Cl.
| | |
|---|---|
| *A61M 5/00* | (2006.01) |
| *A61N 5/06* | (2006.01) |
| *A61N 5/10* | (2006.01) |
| *A61K 31/28* | (2006.01) |
| *A61K 31/30* | (2006.01) |
| *A61K 33/24* | (2019.01) |
| *A61K 41/00* | (2006.01) |
| *A61K 31/282* | (2006.01) |
| *A61K 31/295* | (2006.01) |

(52) U.S. Cl.
CPC ............... *A61N 5/10* (2013.01); *A61K 33/24* (2013.01); *A61K 41/0057* (2013.01); *A61M 5/00* (2013.01); *A61N 5/062* (2013.01); *A61K 31/28* (2013.01); *A61K 31/282* (2013.01); *A61K 31/295* (2013.01); *A61K 31/30* (2013.01); *A61N 2005/1098* (2013.01)

(58) Field of Classification Search
CPC .... A61K 31/28; A61K 31/282; A61K 31/295; A61K 31/30
USPC ............................ 514/185, 492, 499; 424/9.1
See application file for complete search history.

(56) References Cited

U.S. PATENT DOCUMENTS

| | | | |
|---|---|---|---|
| 5,252,720 A | 10/1993 | Sessler et al. | |
| 5,451,576 A | 9/1995 | Sessler et al. | |
| 5,632,970 A | 5/1997 | Sessler et al. | |
| 5,775,339 A | 7/1998 | Woodburn et al. | |
| 5,776,095 A | 7/1998 | Goldenberg | |
| 5,888,997 A | 3/1999 | Sessler et al. | |
| 6,022,526 A | 2/2000 | Woodburn et al. | |
| 6,827,926 B2 | 12/2004 | Robinson et al. | |
| 6,962,910 B2 | 11/2005 | Brewer et al. | |
| 7,612,057 B2 | 11/2009 | Brewer et al. | |
| 8,148,360 B2 | 4/2012 | Brewer et al. | |
| 8,323,694 B2 | 12/2012 | Hainfeld | |
| 8,328,785 B2 | 12/2012 | Bensaoula et al. | |
| 8,445,475 B2 | 5/2013 | Brewer et al. | |
| 8,741,262 B2 | 6/2014 | Ni et al. | |
| 9,737,565 B2* | 8/2017 | Mandel ................. | A61K 33/24 |
| 2005/0112131 A1 | 5/2005 | Pogue et al. | |

FOREIGN PATENT DOCUMENTS

| | | |
|---|---|---|
| WO | 2013158550 A1 | 10/2013 |
| WO | 2014145428 A2 | 9/2014 |
| WO | 2015059379 A1 | 4/2015 |
| WO | 2016116859 A1 | 7/2016 |

OTHER PUBLICATIONS

Benstead et al. (1990). The effect of combined modality treatment with ionising radiation and TPPS-mediated photodynamic therapy on murine tail skin. British Journal of Cancer, 62, 48-53.
Chan et al. (1986). A new ruthenium radiosensitizer: RuCl2(DMSO)2(4-nitroimidazole)2. International Journal of Radiation Oncology Biology Physics, 12(7), 1059-1062.
Chan et al. (1988). Ruthenium (II) complexes of 4-nitroimidazoles: their characterization, solution chemistry, and radiosensitizing activity. Canadian Journal of Chemistry, 66, 117-122.
Chen et al. (2015). Nanoscintillator-mediated X-ray inducible photodynamic therapy for in vivo cancer treatment. Nano Letters, 15(4), 2249-2256.
Chen et al. (2006). Using nanoparticles to enable simultaneous radiation and photodynamic therapies for cancer treatment. Journal of Nanoscience and Nanotechnology, 6(4), 1159-1166.
Cheng et al. (2015). Bottom-Up Synthesis of Metal-Ion-Doped WS2 Nanoflakes for Cancer Theranostics. ACS Nano, 9(11), 11090-11101.
Chibber et al. (1985). The interaction between radiation and complexes of cis-Pt(II) and Rh(II): studies at the molecular and cellular level. Int J Radiat Biol Relat Stud Phys Chem Med, 48(4):513-524.
Deng et al. (2015). Rational Design of Ruthenium Complexes Containing 2,6-Bis(benzimidazolyl)pyridine derivatives with radiosensitization activity by enhancing p53 activation. ChemMedChem, 10, 991-998.
Ehmer et al. (2016). Control of Proliferation and Cancer Growth by the Hippo Signaling Pathway. American Association for Cancer Research, 14, 127-140.

(Continued)

*Primary Examiner* — Kevin E Weddington
(74) *Attorney, Agent, or Firm* — Caesar Rivise, PC

(57) ABSTRACT

A method for destroying cells and/or microorganisms in an organism includes the following steps: (a) administering to the organism a composition including a photodynamic compound containing at least one transition metal; and (b) irradiating the photodynamic compound in the organism with electromagnetic radiation, wherein the electromagnetic radiation includes ionizing radiation and is effective to activate the photodynamic compound to destroy at least one of the cells and the microorganisms in the organism. The ionizing radiation is preferably X-rays and/or gamma rays. The non-ionizing radiation is preferably light in the range from 600-950 nm.

13 Claims, 4 Drawing Sheets

(56) References Cited

OTHER PUBLICATIONS

Khan et al. (2012). Gold nanoparticles enhance methylene blue-induced photodynamic therapy: a novel therapeutic approach to inhibit Candida albicans biofilm. International Journal of Nanomedicine. 7, 3245-3257.
Montazerabadi et al. (2012). The effects of combined treatment with ionizing radiation and indocyanine green-mediated photodynamic therapy on breast cancer cells. Journal of Photochemistry and Photobiology B: Biology, 109, 42-49.
Ostrowski et al. (2009). Metal complexes as photochemical nitric oxide precursors: Potential applications in the treatment of tumors. Dalton Transactions, 10660-10669.
Rothikamm et al. (2003). Evidence for a lack of DNA double-strand break repair in human cells exposed to very low x-ray doses. PNAS, 100(9), 5057-5062.
Sazgarnia et al. (2013). In vitro survival of MCF-7 breast cancer cells following combined treatment with ionizing radiation and mitoxantrone-mediated photodynamic therapy. Photodiagnosis Photodynamic Therapy, 10, 72-78.
Sazgarnia et al. (2013). Photosensitizing and radiosensitizing effects of mitoxantrone: combined chemo-, photo-, and radiotherapy of DFW human melanoma cells. Lasers Med Sci, 1-7.
Wang et al. (2015). Gold nanostars mediated combined photothermal and photodynamic therapy and X-ray imaging for cancer theranostic applications. Journal of Biomaterials Applications, 30(5), 547-557.
Wang et al. (2010). Tumor cell apoptosis induced by nanoparticle conjugate in combination with radiation therapy. Nanotechnology. 21(47), 475103: 1-7.
Yong et al. (2014). WS2 nanosheet as a new photosensitizer carrier for combined photodynamic and photothermal therapy of cancer cells. Nanoscale, 6, 10394-10403.

\* cited by examiner 10 min 30 min 60 min 120 min 240 min

PHOTODYNAMIC COMPOUNDS AND METHODS FOR ACTIVATING THEM USING IONIZING RADIATION AND/OR OTHER ELECTROMAGNETIC RADIATION FOR THERAPY AND/OR DIAGNOSTICS

BACKGROUND OF THE INVENTION

1. Field of Invention

This invention relates to the use of electromagnetic radiation to activate metal-based coordination complexes, and more particularly to diagnostic and therapeutic methods comprising the use of ionizing radiation to activate metal-based coordination complexes.

2. Description of Related Art

Photodynamic Therapy

Photodynamic therapy (PDT) is currently an active area of research for the treatment of diseases associated with hyperproliferating cells such as cancer and non-malignant lesions. The development of new photodynamic compounds (PDCs or photosensitizers, PSs) for photodynamic therapy (PDT) has been increasingly focused on metallosupramolecular complexes derived from metals. For example, WO 2013158550 A1 and WO 2014145428 A2 disclose metal-based PDCs useful as in vivo diagnostic agents, as therapeutic agents for treating or preventing diseases that involve unwanted and/or hyperproliferating cell etiology, including cancer, as agents for treating infectious diseases, and as agents for pathogen disinfection and/or sterilization. U.S. Pat. Nos. 6,962,910, 7,612,057, 8,445,475 and 8,148,360 disclose supramolecular metal complexes capable of cleaving DNA when irradiated low energy visible light with or without molecular oxygen.

Chan et al. "A new ruthenium radiosensitizer: $RuCl_2$ $(DMSO)_2$(4-nitroimidazole)$_2$." International Journal of Radiation Oncology Biology Physics, Vol. 12, No. 7 (1986): 1059-1062 and Chan et al. "Ruthenium (II) complexes of 4-nitroimidazoles: their characterization, solution chemistry, and radiosensitizing activity." Canadian Journal of Chemistry, Vol. 66, No. 1 (1988): 117-122 disclose ruthenium-based radiophotosensitizers.

Delivery of electromagnetic radiation effective to activate PDCs can pose a challenge. Visible light PDT and UV light PDT have limited penetration depths, which precludes activation of photodynamic compounds in deep tumors and requires invasive illumination devices. Shaping the PDT-high dose field with a steep gradient at the edge of the clinical treatment volume is currently limited by the gradient of the effective light attenuation in tissue.

WO 2015059379 A1 purports to address such limitations of conventional PDT by providing a molecular conjugate comprising a radioluminescent molecule and a photosensitizer, and/or radio-contrast molecules and a photosensitizer for various X-ray-based imaging techniques, including, but not limited to computed tomography (CT) radiography and fluoroscopy, the radioluminescent molecule being suitable for absorbing an X-ray with energy higher than an absorption threshold and for emitting luminescent radiation in the visible domain, and the photosensitizer being suitable for absorbing said luminescent radiation and producing singlet oxygen.

US 20050112131 A1 discloses a therapeutic method comprising PDT and radiation therapy, wherein the PDT maximizes oxygen production and distribution such that the efficacy of the radiation therapy is enhanced.

X-Rays

The conventional use of X-rays is currently in diagnostic procedures, particularly for transmission based X-rays and Computerized Tomography ("CT") scans. With the current advantage of solid state detectors, the average radiation dose is as low as 0.7 mGy for abdominal X-rays, 8.0 mGy for abdominal CT scans, 6 mGy for pelvic CT scans, and 14 mGy for selective CT scans of the abdomen and the pelvis (http://www.xrayrisk.com/calculator/calculator.php). These diagnostic procedures increase cancer risk for a 50-year-old person typically by much less than 0.1%. The use of X-rays for therapeutic applications is no longer applicable as higher energy ionizing radiation (6 MeV) is currently used for radiation therapy.

X-rays can damage DNA by causing double-strand breaks ("DSBs"). In vitro experiments show that DSBs are generated at a rate of 35 DSBs per cell per Gray (Rothkamm et al., "Evidence for a lack of DNA double-strand break repair in human cells exposed to very low x-ray doses." Proc Natl Acad Sci USA. 2003 Apr. 29; 100(9):5057-62. Epub 2003 Apr. 4) and remove epigenetic markers of the DNA which regulate the gene expression (Ehmer et al., "Control of Proliferation and Cancer Growth by the Hippo Signaling Pathway." Mol Cancer Res, 2016 14:127-140; Published OnlineFirst Oct. 2, 2015; doi:10.1158/1541-7786). Most DSBs are repaired within 24 h but 25% of the repaired strands are repaired incorrectly and about 20% of fibroblast cells that were exposed to 200 mGy died within 4 days post exposure.

X-rays have been used in combination with light to overcome limited light penetration depth during PDT is the use of nanoparticles conjugated with photosensitizers. Under exposure to X-rays, the nanoparticles emit light that activates the photosensitizers (Chen et al., "Using nanoparticles to enable simultaneous radiation and photodynamic therapies for cancer treatment." J. Nanosci. Nanotech. 6 (2006), 1159-1166; Wang et al., "Tumor cell apoptosis induced by nanoparticle conjugate in combination with radiation therapy." Nanotechnology. 2010 Nov. 26; 21(47): 475103. doi: 10.1088/0957-4484/21/47/475103. Epub 2010 Oct. 29). This approach allows fine regulation of the final PDT effect (Chen et al., "Nanoscintillator-mediated X-ray inducible photodynamic therapy for in vivo cancer treatment." Nano Lett. 2015 Apr. 8; 15(4):2249-56. doi: 10.1021/nl504044p. Epub 2015 Mar. 12). Moreover, successful effect of nanoparticle-photosensitizer combination under ionizing radiation was possible at the radiation dose that was not effective alone (Wang et al., 2010). Nanoparticles alone are capable for both photothermal and photodynamic effect upon activation by near infrared irradiation (Wang et al., "Gold nanostars mediated combined photothermal and photodynamic therapy and X-ray imaging for cancer theranostic applications." J Biomater Appl. 2015 November; 30(5):547-57. doi: 10.1177/0885328215594481. Epub 2015 Jul. 21). A number of patents consider the use of nanoparticles (with or without transition metals conjugated) and photosensitizers (in consequent separate administration) for combined simultaneous treatment with ionizing radiation and PDT (U.S. Pat. No. 8,328,785). It is noteworthy that nanoparticles on their own can also be irradiated with infrared light to produce therapeutic photothermal effects (U.S. Pat. No. 8,323,694).

Some photosensitizer molecules can be activated by X-ray radiation that can be combined with photodynamic therapy, as demonstrated for mitoxantrone (Sazgarnia et al., "Photosensitizing and radiosensitizing effects of mitoxantrone: combined chemo-, photo-, and radiotherapy of DFW human melanoma cells." Lasers Med Sci. 2013 November; 28(6):1533-9. doi: 10.1007/s10103-013-1275-8. Epub 2013 Feb. 1) and indocyanine green (Montazerabadi et al., "The effects of combined treatment with ionizing radiation and indocyanine green-mediated photodynamic therapy on breast cancer cells." J Photochem Photobiol B. 2012 Apr. 2; 109:42-9. doi: 10.1016/j.jphotobiol.2012.01.004. Epub 2012 Jan. 28). Texaphyrins complexed with metals are considered in some patents as promising photosensitizers for combined treatment by ionizing radiation and PDT (U.S. Pat. No. 5,632,970) utilizing inherent radiosensitization properties of the texaphyrins (U.S. Pat. No. 5,632,970).

Use of Transition Metals in Compounds

The use of transition metal ("TM") based compounds for therapy is increasing (Cheng et al., "Bottom-Up Synthesis of Metal-Ion-Doped WS2 Nanoflakes for Cancer Theranostics." ACS Nano. 2015 Nov. 24; 9(11):11090-101. doi: 10.1021/acsnano.5b04606. Epub 2015 Oct. 9); whereby, the standard aim for the inclusion of the TM is to increase functionality, for example, through their strong near-infrared ("NIR") absorbance and X-ray attenuation ability enabling contrasts in photoacoustic ("PA") imaging and computed tomography ("CT"). In addition, Gd(III) doping offers the nanostructure a paramagnetic property for magnetic resonance imaging ("MRI").

Ionizing Radiation Sensitizers: Role of Metal

Metal complexes have been suggested as photon induced nitric oxide ("NO") donors, which in turn are known as gamma ray sensitizers (Ostrowski et al., "Metal complexes as photochemical nitric oxide precursors: Potential applications in the treatment of tumors." Dalton Transactions, 2009, 48, 10660-10669). Investigating the interaction of platinum and other transition metal based chemosensitizers dates back to the 1980s. In particular, for hypoxic cells, metal complexes containing nitroimidazoles as ligands have been shown to act as radiosensitizers albeit this effect was transient in oxygenated cells (Chibber et al., "The interaction between radiation and complexes of cis-Pt(II) and Rh(II): studies at the molecular and cellular level." Int J Radiat Biol Relat Stud Phys Chem Med. 1985 October; 48(4):513-24).

Metals proposed for use in photosensitizers for X-ray & PDT combined treatment are divalent and trivalent metal ions (U.S. Pat. No. 5,451,576) such as Ca(II), Mn(II), Co(II), Ni(II), Zn(II), Cd(II), Hg(II), Fe(II), Sm(II), UO.sub.2(II), Mn(III), Co(III), Ni(III), Fe(III), Ho(III), Ce(III), Y(III), In(III), Pr(III), Nd(III), Sc(III), Sm(III), Eu(III), Gd(III), Tb(III), Dy(III), Er(III), Tm(III), Yb(III), Lu(III), La(III), and U(III) (U.S. Pat. Nos. 5,888,997, 5,252,720) as well as gallium (U.S. Pat. No. 6,827,926). The usable metals include transition metals of groups IB, IIB, IIIB, IVB, VB, VIB, VIIB and VIII (U.S. Pat. No. 8,328,785). Metals supposed to be diamagnetic (U.S. Pat. No. 5,632,970) such as Lu(III), La(III), In(III), Y(III), Dy(III), Zn(II), or Cd(II), and Lu(III) are considered most preferable (U.S. Pat. No. 5,775,339).

On the other hand, for the texaphyrins, the metal is not essential to the radiosensitization properties of the complex (U.S. Pat. No. 5,632,970).

Transition Metals: Role of Ligands

In recent years, it has also become more evident that the ligands are quintessential for implementation of the transition metals efficacy in initiating apoptosis in cancer cells (Deng et al., "Rational Design of Ruthenium Complexes Containing 2,6-Bis(benzimidazolyl)pyridine Derivatives with Radiosensitization Activity by Enhancing p53 Activation. Chem Med Chem." 2015 June; 10(6):991-8. doi: 10.1002/cmdc.201500127. Epub 2015 Apr. 27). The Ru-based complexes, in the mentioned study, amplified X-ray induced Reactive Oxygen Species ("ROS") generation and consequent DNA damage resulting in cell cycle disruption and induction of apoptosis. The effect in cell growth inhibition was; however, relatively small, not exceeding 2.5-fold for one of the three compounds and less than 2-fold for the other two compounds.

Synergy

Among the advantages of the combined X-ray and light treatment is a synergistic effect that is greater than the additive effect (simply a sum of separate X-ray and light treatment). Light PDT can be followed by or combined with ionizing radiation (U.S. Pat. No. 5,632,970). Synergism was observed for mitoxantrone (Sazgarnia et al., "In vitro survival of MCF-7 breast cancer cells following combined treatment with ionizing radiation and mitoxantrone-mediated photodynamic therapy." Photodiagnosis Photodyn Ther. 2013 February; 10(1):72-8. doi: 10.1016/j.pdpdt.2012.06.001. Epub 2012 Jul. 1). Indocyanine was not effective at ionizing radiation alone but very effective at combined treatment, suggesting a synergistic effect of the light and X-rays combination (Montazerabadi et al., 2012).

Safety

Additive effects ensure greater safety of combined treatment by allowing lower doses of radiation during the treatment (Chen & Zhang, 2006; U.S. Pat. No. 5,632,970) or reduction of adverse effects of photosensitizer (Sazgarnia et al., 2013).

Imaging & Therapy

A mixed localization and therapy modality of the therapeutic agents is conventionally achieved by the use of radioisotopes, including X-ray emitters (U.S. Pat. No. 5,776, 095). However, the use of radiopaque properties with no inherent radioactivity is increasingly proposed. Labelling of non-photosensitizers able to induce tumor necrosis with radiopaque material allows use as X-ray contrast agents (U.S. Pat. No. 8,741,262). A number of patents consider the use of nanoparticles, alone or combined with other photosensitizers for imaging of therapeutic targets, together with the cell killing potential upon irradiation via photothermal or photodynamic mechanisms (U.S. Pat. Nos. 8,328,785; 8,323,694). This not always suggests the use of the same kind of irradiation for both localization and therapy: X-ray for detection and subsequent infrared irradiation for induction of photothermal effect (U.S. Pat. No. 8,323,694). It is noteworthy that nanoparticles on their own were proposed both for imaging detection and as mediators of both photothermal and photodynamic effect (Yong et al., "WS2 nanosheet as a new photosensitizer carrier for combined photodynamic and photothermal therapy of cancer cells. Nanoscale. 2014 Sep. 7; 6(17):10394-403. doi: 10.1039/c4nr02453b"; Khan et al., "Gold nanoparticles enhance methylene blue-induced photodynamic therapy: a novel therapeutic approach to inhibit *Candida albicans* biofilm." Int J Nanomedicine. 2012; 7:3245-57. doi: 10.2147/IJN.S31219. Epub 2012 Jun. 29).

However, direct use of photosensitizers for both localization and therapy is also underway. Texaphyrin metal complexes were proposed for MRI detection, with subsequent PDT or X-ray treatment (U.S. Pat. Nos. 5,252,720, 5,451, 576). X-ray detection of texaphyrins was also proposed (U.S. Pat. No. 6,022,526), with subsequent radiation sensitization (U.S. Pat. No. 5,632,970). In a more complex setting, two related but distinct molecules were proposed to be used: texaphyrin detectable by fluorescent spectroscopy (non-metallated or complexed with a diamagnetic metal), MRI (complexed with paramagnetic metal), gamma scanning (complexed with gamma emitting metal) or by diagnostic X-rays (complexed with metals) and photosensitive texaphyrin (metal free or complexed with diamagnetic metal) to ensure both radiation sensitization and photodynamic therapy (U.S. Pat. No. 5,888,997). Also, metallotetrapyrrolic compounds (particularly porphyrins and azaporphyrins complexed with gallium) were considered as useful both for photodetection and phototherapy (U.S. Pat. No. 6,827,926).

Despite the foregoing developments, it is still desired to provide improved compositions and methods for conducting PDT, which comprise the use of x-ray radiation.

SUMMARY OF THE INVENTION

A first aspect of the invention comprises a method for destroying cells and/or microorganisms in an organism, said method comprising: administering to the organism a composition comprising a photodynamic compound containing at least one transition metal; and irradiating the photodynamic compound in the organism with electromagnetic radiation, wherein the electromagnetic radiation comprises ionizing radiation and is effective to activate the photodynamic compound to destroy at least one of the cells and the microorganisms in the organism.

In certain embodiments, the cells are hyperproliferating cells.

In certain embodiments, the microorganisms are at least one member selected from the group consisting of bacteria, viruses and fungi.

In certain embodiments, the organism is a human.

In certain embodiments, the composition is adminstered by topical, oral, buccal, intravenous, intramuscular, intraarterial, intramedullary, intrathecal, intraventricular, transdermal, subcutaneous, intraperitoneal, intranasal, enteral, topical, sublingual, vaginal, ophthalmic, pulmonary or rectal routes.

In certain embodiments, the composition is pharmaceutically acceptable and further comprises at least one pharmaceutically acceptable carrier, excipient or diluent.

In certain embodiments, the composition further comprises a metal-binding glycoprotein, which is preferably transferrin.

In certain embodiments, the irradiating step comprises irradiating the organism with non-ionizing radiation in a range from 600-950 nm and with at least one of X-rays and Gamma rays.

In certain embodiments, the irradiating step comprises irradiating the organism with 0.1 to 100 Gy of X-ray radiation and with non-ionizing radiation in a range from 600-950 nm. In these embodiments, it is preferred that the organism is irradiated with the X-ray radiation and the non-ionizing radiation in an order and at a power which are synergistically effective to: (a) inhibit proliferation of hyperproliferating cells in the organism and/or (b) destroy microorganisms in the organism.

In certain embodiments, the method is conducted without a molecular conjugate comprising a radioluminescent molecule and a photosensitizer.

In certain embodiments, the photodynamic compound is a metallosupramolecular complex containing at least one transition metal selected from the group consisting of osmium, manganese, molybdenum, rhenium, ruthenium, iron, cobalt, rhodium, iridium, nickel, platinum, and copper.

In certain embodiments, the photodynamic compound has the formula (I):

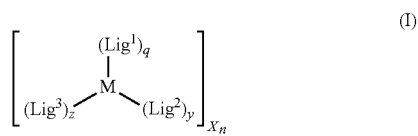

including hydrates, solvates, pharmaceutically acceptable salts, prodrugs and complexes thereof, wherein:

M at each occurrence is independently selected from the group consisting of osmium, ruthenium and rhodium;

X is selected from the group consisting of Cl$^-$, PF$_6^-$, BC, BF$_4^-$, ClO$_4^-$, CF$_3$SO$_3^-$, and SO$_4^{-2}$;

n=0, 1, 2, 3, 4, or 5;

q is independently at each occurrence 0, 1, or 2;

y is independently at each occurrence 0, 1, or 2;

z is independently at each occurrence 1, 2, or 3;

Lig$^1$ is a bidentate ligand that at each occurrence is each independently selected from the group consisting of

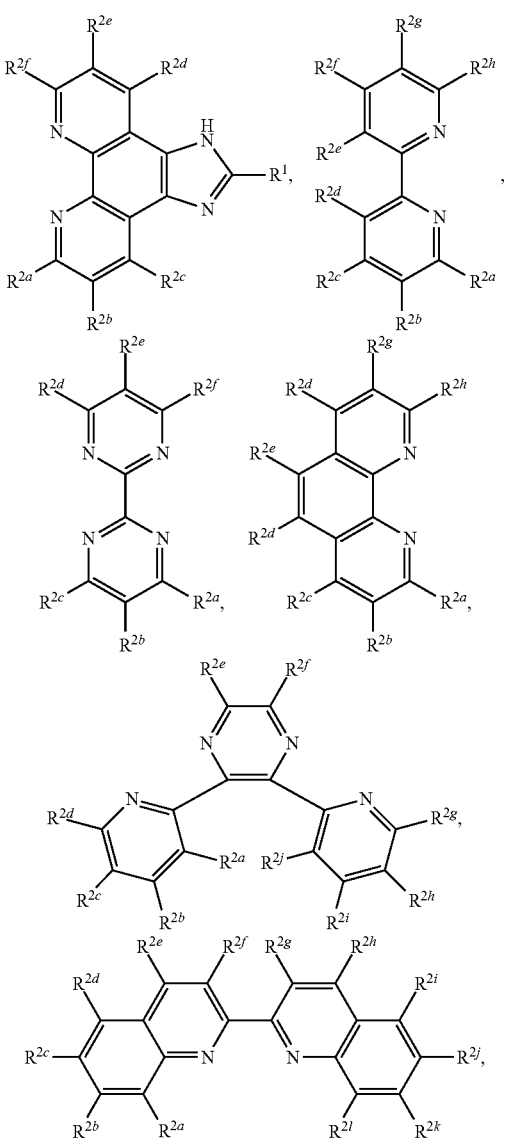

-continued
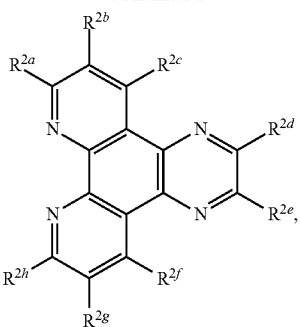
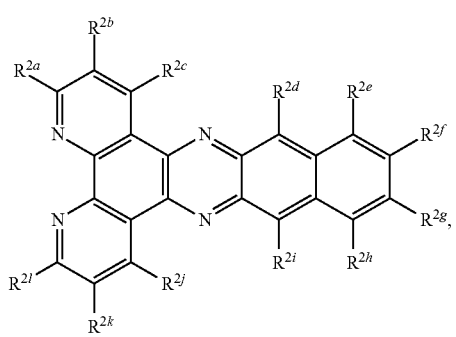
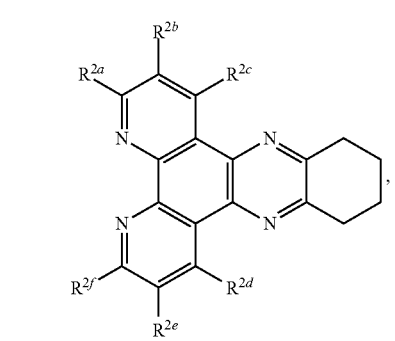
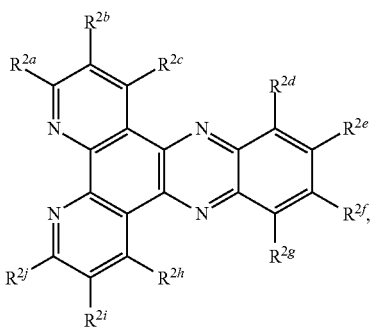
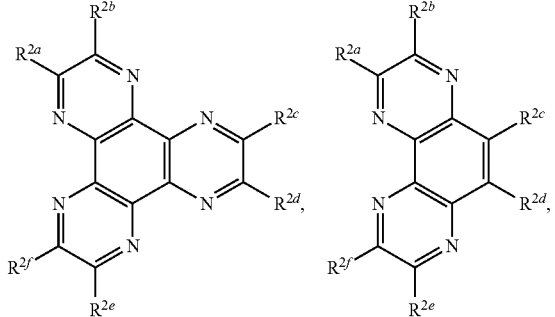
-continued
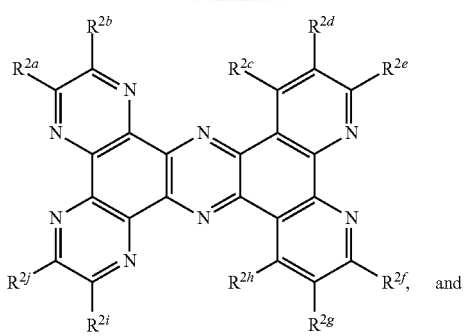
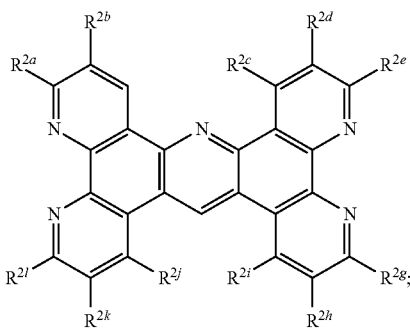
Lig² is a bidentate ligand that at each occurrence is each independently selected from the group consisting of
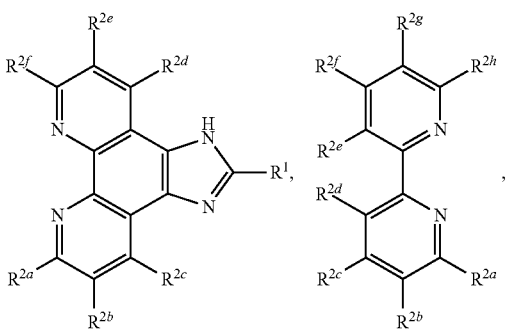
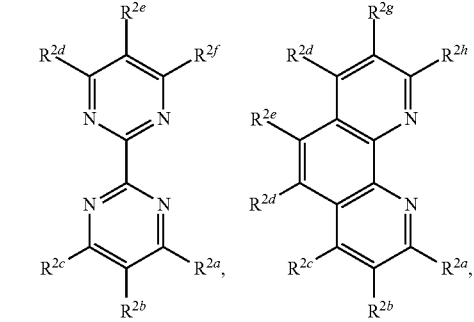

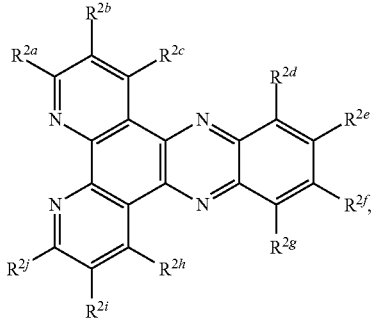
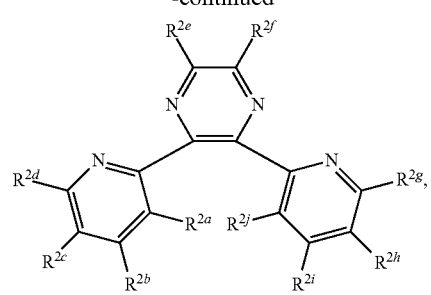
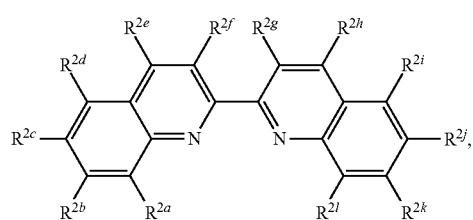
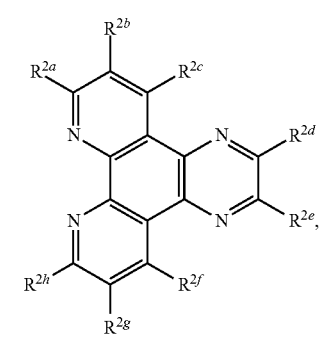
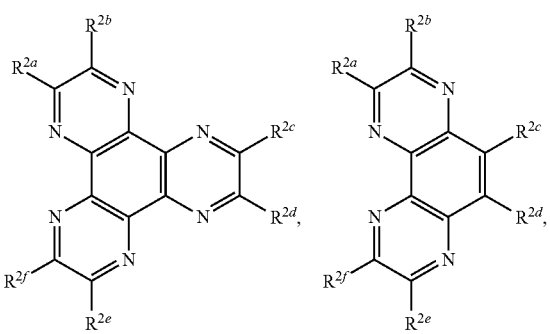
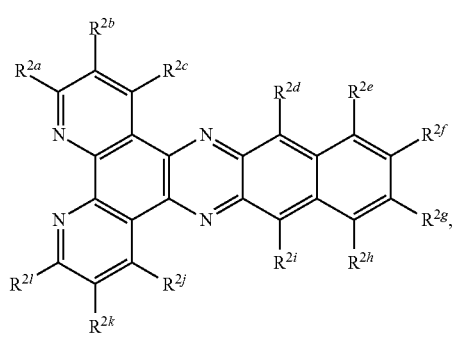
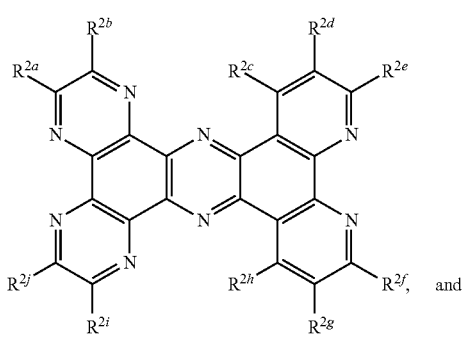
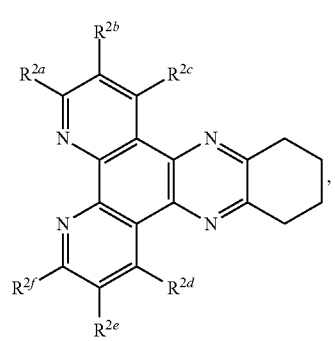
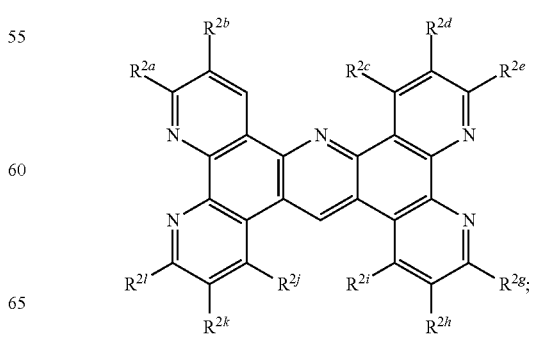

Lig³ is a bidentate ligand that at each occurrence is each independently selected from the group consisting of
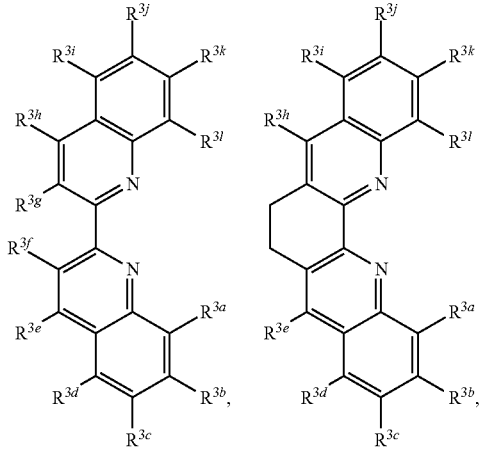
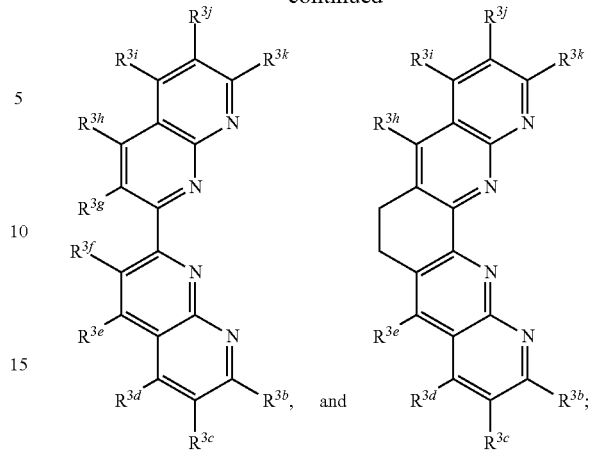
R¹ is selected from the group consisting of hydrogen, optionally substituted phenyl, optionally substituted aryl, optionally substituted heteroaryl, 4-pyridyl, 3-pyridyl, 2-thiazole, 2-pyrolyl, 2-furanyl,
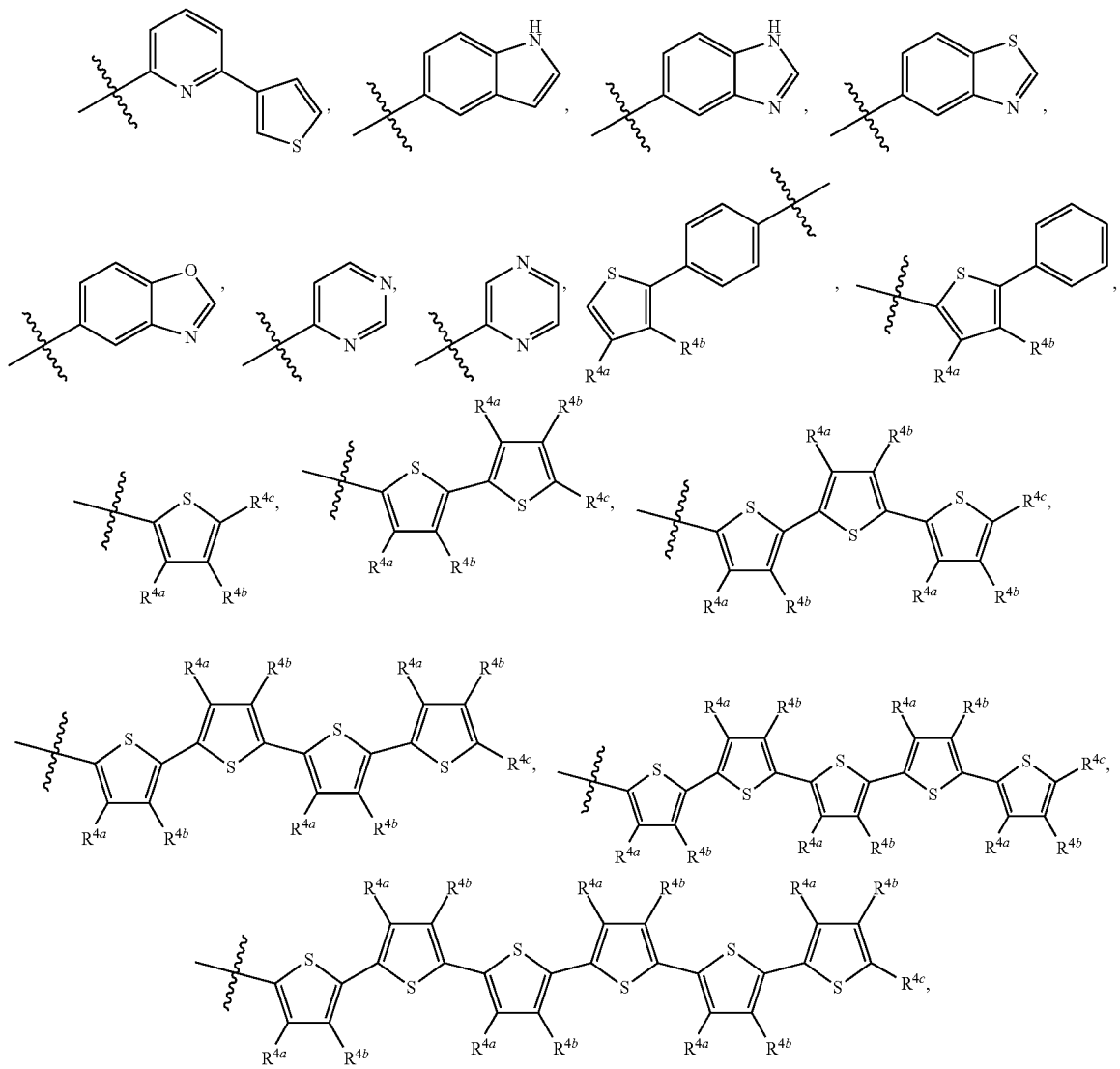

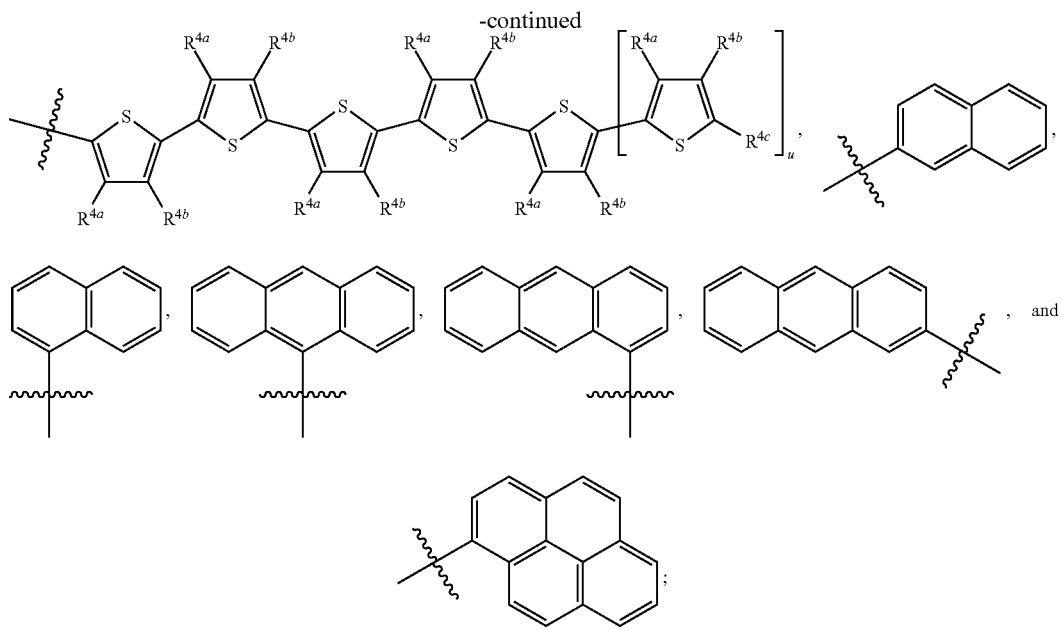

u is an integer;

$R^{2a}$, $R^{2b}$, $R^{2c}$, $R^{2d}$, $R^{2e}$, $R^{2f}$, $R^{2g}$, $R^{2h}$, $R^{2i}$, $R^{2j}$, $R^{2k}$, and $R^{2l}$ at each occurrence are each independently selected from the group consisting of hydrogen, $C_{1-6}$ optionally substituted alkyl, $C_{1-6}$ optionally substituted branched alkyl, $C_{3-7}$ optionally substituted cycloalkyl, $C_{1-6}$ optionally substituted haloalkyl, $C_{1-6}$ optionally substituted alkoxy, $CO_2R^5$, $CONR^6_2$, $NR^7_2$, $SO_3H$, sulfate, sulfonate, optionally substituted aryl, optionally substituted aryloxy, optionally substituted heteroaryl, and optionally substituted heterocycle;

$R^{3a}$, $R^{3b}$, $R^{3c}$, $R^{3d}$, $R^{3e}$, $R^{3f}$, $R^{3g}$, $R^{3h}$, $R^{3i}$, $R^{3j}$, $R^{3k}$, and $R^{3l}$ at each occurrence are each independently selected from the group consisting of hydrogen, $C_{1-6}$ optionally substituted alkyl, $C_{1-6}$ optionally substituted branched alkyl, $C_{1-6}$ optionally substituted haloalkyl, $C_{1-6}$ optionally substituted alkoxy, optionally substituted phenyl, and $CO_2R^8$;

$R^{4a}$, $R^{4b}$, and $R^{4c}$ at each occurrence are each independently selected from the group consisting of hydrogen, $C_{1-6}$ optionally substituted alkyl, $C_{1-6}$ optionally substituted branched alkyl, $C_{1-6}$ optionally substituted cycloalkyl, $C_{1-6}$ optionally substituted haloalkyl, $C_{1-6}$ optionally substituted alkoxy, $CO_2R^5$, $CONR^6_2$, $NR^7_2$, sulfate, sulfonate, optionally substituted aryl, optionally substituted aryloxy, optionally substituted heteroaryl, and optionally substituted heterocycle;

$R^{4a}$ and $R^{4b}$ at each occurrence on a thiophene ring are taken together with the atom to which they are bound to form an optionally substituted ring having from 6 ring atoms containing 2 oxygen atoms;

$R^5$ at each occurrence are each independently selected from the group consisting of hydrogen and optionally substituted alkyl;

$R^6$ at each occurrence are each independently selected from the group consisting of hydrogen and optionally substituted alkyl;

$R^7$ at each occurrence are each independently selected from the group consisting of hydrogen and optionally substituted alkyl; and $R^8$ at each occurrence are each independently selected from the group consisting of hydrogen and optionally substituted alkyl.

In certain embodiments, the photodynamic compound has the formula (VI):

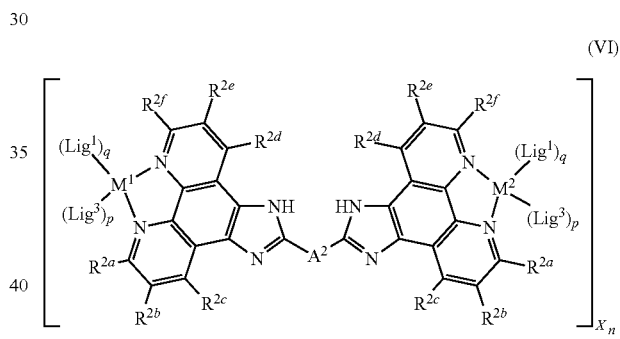

including hydrates, solvates, pharmaceutically acceptable salts, prodrugs and complexes thereof wherein;

$M^1$ and $M^2$ at each occurrence is independently selected from the group consisting of osmium, manganese, molybdenum, rhenium, ruthenium, iron, cobalt, rhodium, iridium, nickel, platinum, and copper;

$A^2$ is selected from the group consisting of

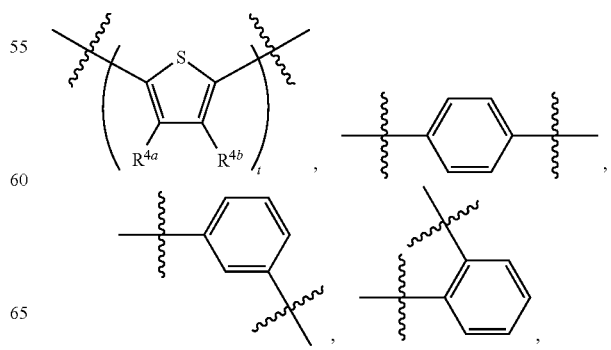

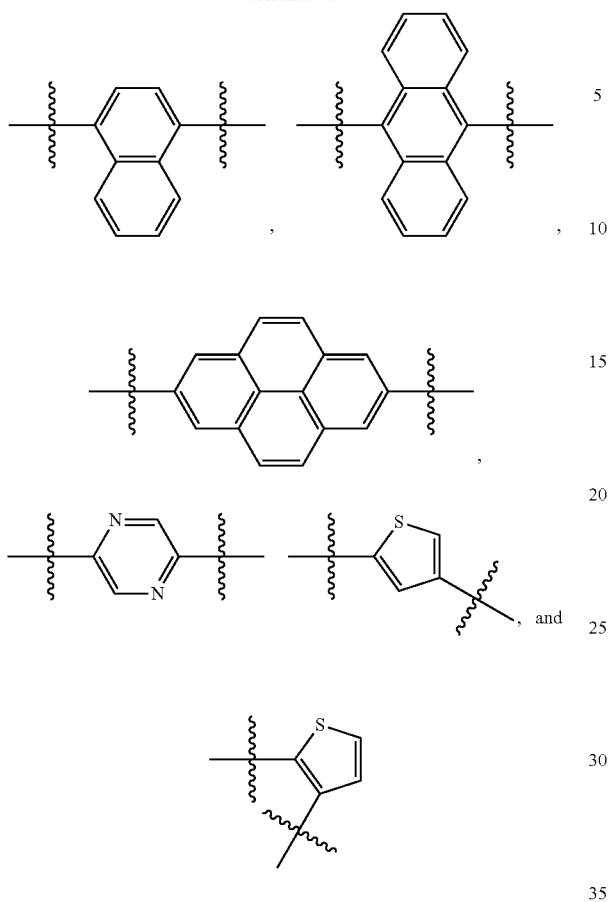
t is an integer.
In certain embodiments, the photodynamic compound has the formula (VIIa)
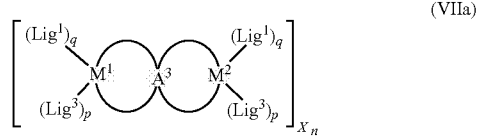
(VIIa)
including hydrates, solvates, pharmaceutically acceptable salts, prodrugs and complexes thereof wherein:
$A^3$ is selected from the group consisting of
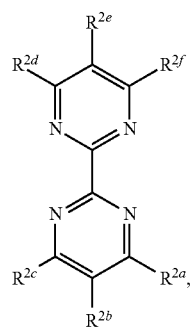
$Lig^1$ is a bidentate ligand that at each occurrence is each independently selected from the group consisting of
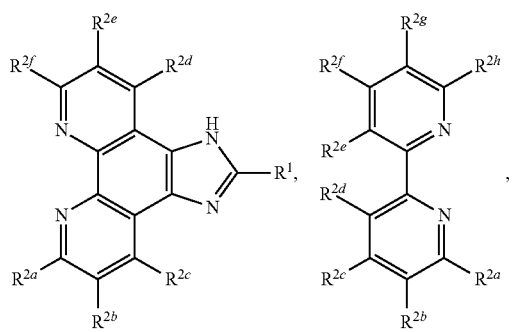

-continued
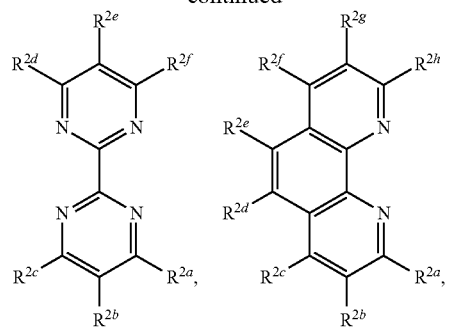
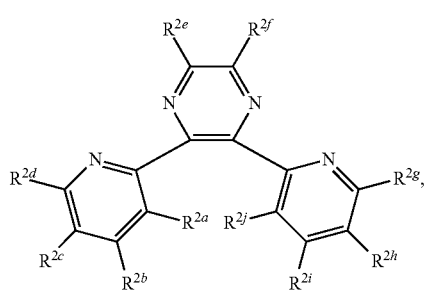
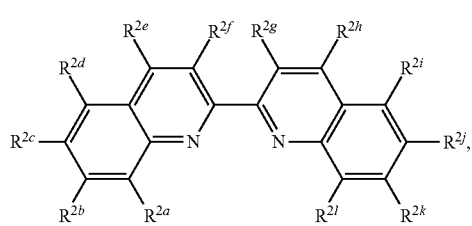
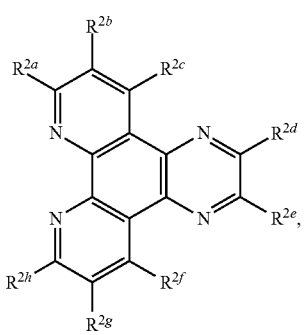
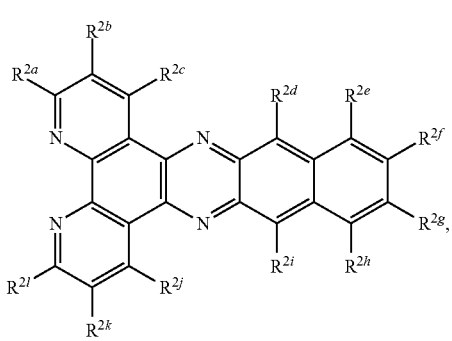
-continued
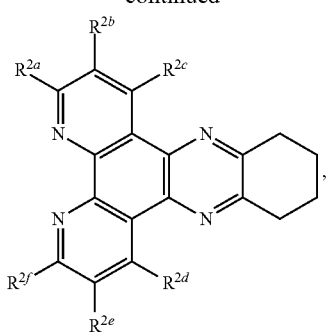
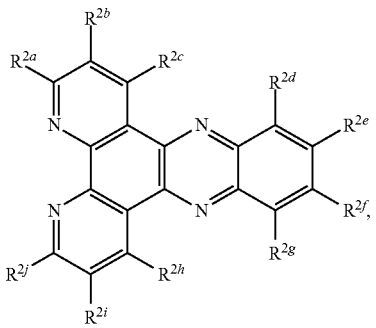
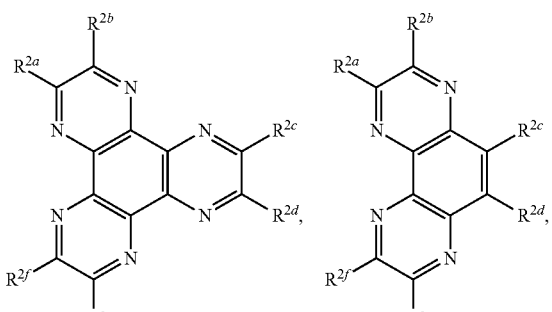
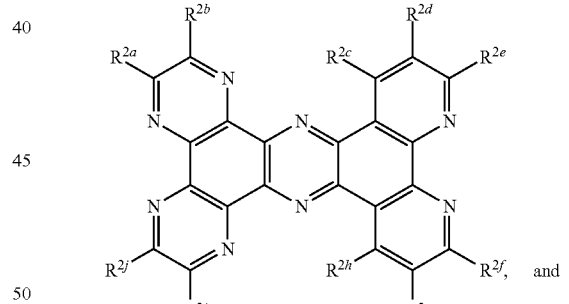, and
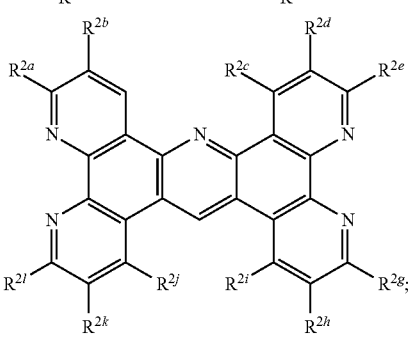;
Lig³ is a bidentate ligand that at each occurrence is each independently selected from the group consisting of

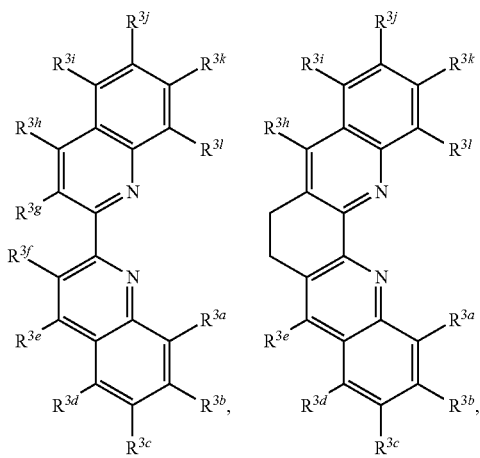
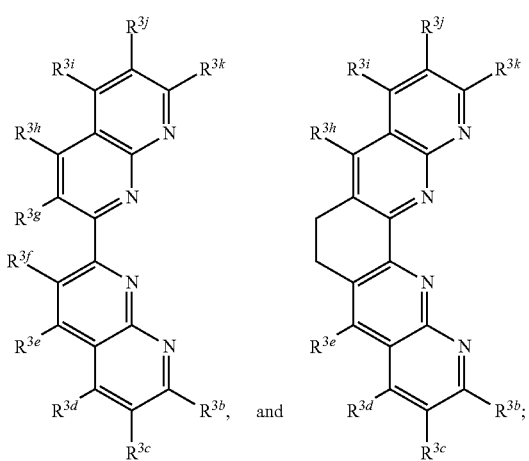
$R^1$ is selected from the group consisting of hydrogen, optionally substituted phenyl, optionally substituted aryl, optionally substituted heteroaryl, 4-pyridyl, 3-pyridyl, 2-thiazole, 2-pyrolyl, 2-furanyl,
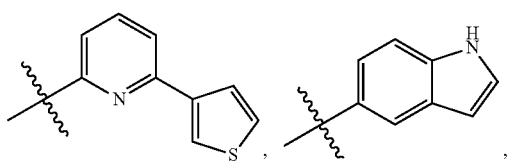
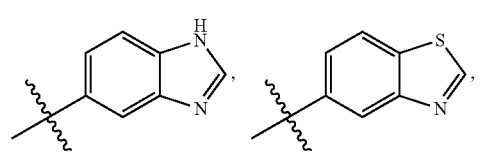
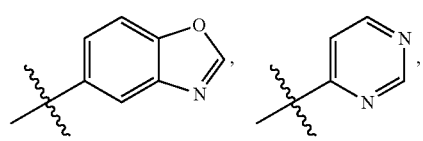
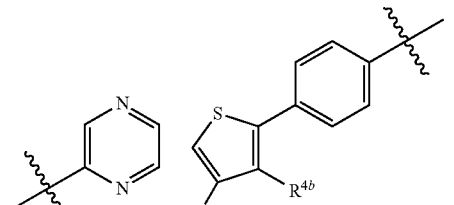
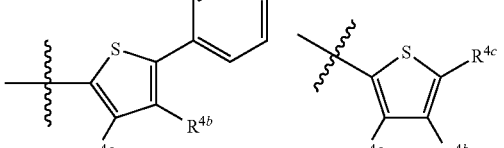
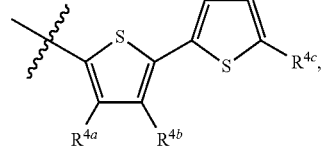
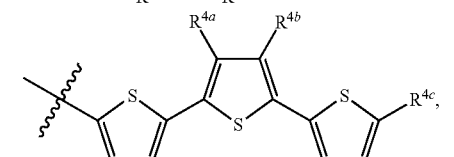
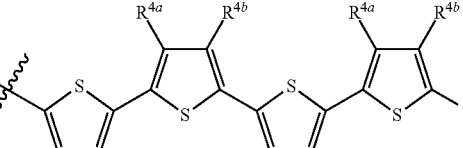
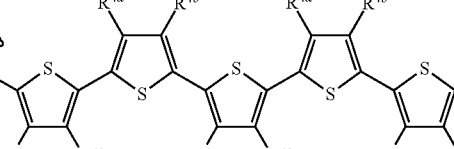
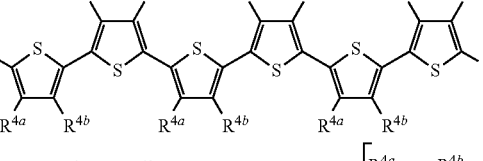
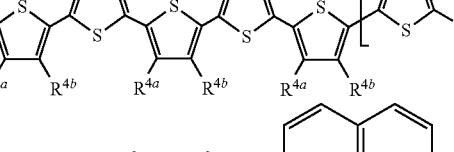
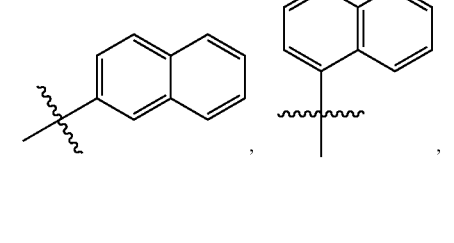

-continued

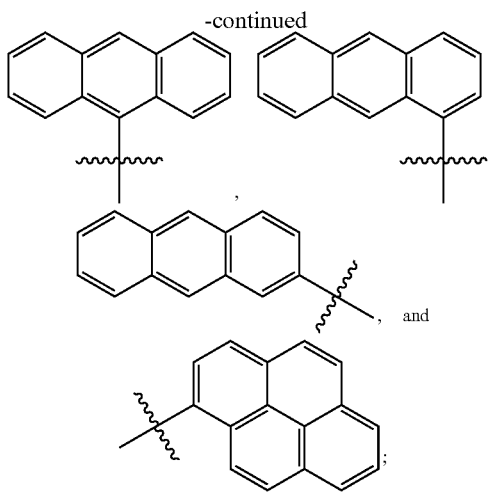

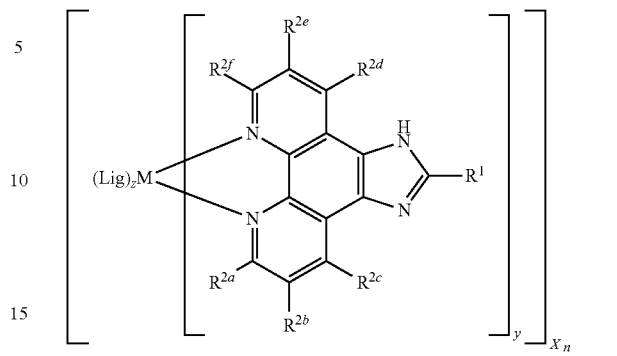

u is an integer;
$R^{2a}$, $R^{2b}$, $R^{2c}$, $R^{2d}$, $R^{2e}$, $R^{2f}$, $R^{2g}$, $R^{2h}$, $R^{2i}$, $R^{2j}$, $R^{2k}$, and $R^{2l}$ at each occurrence are each independently selected from the group consisting of hydrogen, $C_{1-6}$ optionally substituted alkyl, $C_{1-6}$ optionally substituted branched alkyl, $C_{3-7}$ optionally substituted cycloalkyl, $C_{1-6}$ optionally substituted haloalkyl, $C_{1-6}$ optionally substituted alkoxy, $CO_2R^5$, $CONR^6_2$, $NR^7_2$, $SO_3H$, sulfate, sulfonate, optionally substituted aryl, optionally substituted aryloxy, optionally substituted heteroaryl, and optionally substituted heterocycle;
$R^{3a}$, $R^{3b}$, $R^{3c}$, $R^{3d}$, $R^{3e}$, $R^{3f}$, $R^{3g}$, $R^{3h}$, $R^{3i}$, $R^{3j}$, $R^{3k}$, and $R^{3l}$ at each occurrence are each independently selected from the group consisting of hydrogen, $C_{1-6}$ optionally substituted alkyl, $C_{1-6}$ optionally substituted branched alkyl, $C_{1-6}$ optionally substituted haloalkyl, $C_{1-6}$ optionally substituted alkoxy, optionally substituted phenyl, and $CO_2R^8$;
$R^{4a}$, $R^{4b}$, and $R^{4c}$ at each occurrence are each independently selected from the group consisting of hydrogen, $C_{1-6}$ optionally substituted alkyl, $C_{1-6}$ optionally substituted branched alkyl, $C_{1-6}$ optionally substituted cycloalkyl, $C_{1-6}$ optionally substituted haloalkyl, $C_{1-6}$ optionally substituted alkoxy, $CO_2R^5$, $CONR^6_2$, $NR^7_2$, sulfate, sulfonate, optionally substituted aryl, optionally substituted aryloxy, optionally substituted heteroaryl, and optionally substituted heterocycle;
$R^{4a}$ and $R^{14b}$ at each occurrence on a thiophene ring are taken together with the atom to which they are bound to form an optionally substituted ring having from 6 ring atoms containing 2 oxygen atoms;
$R^5$ at each occurrence are each independently selected from the group consisting of hydrogen and optionally substituted alkyl;
$R^6$ at each occurrence are each independently selected from the group consisting of hydrogen and optionally substituted alkyl;
$R^7$ at each occurrence are each independently selected from the group consisting of hydrogen and optionally substituted alkyl; and
$R^8$ at each occurrence are each independently selected from the group consisting of hydrogen and optionally substituted alkyl
p is independently at each occurrence 0, 1, or 2;
q is independently at each occurrence 0, 1, or 2; and
n is 0, 1, 2, 3, 4, or 5.

In certain embodiments, the photodynamic compound has the formula (II)

including hydrates, solvates, pharmaceutically acceptable salts, prodrugs and complexes thereof, wherein:

M is selected from the group consisting of manganese, molybdenum, rhenium, iron, ruthenium, osmium, cobalt, rhodium, iridium, nickel, platinum, and copper;

X is selected from the group consisting of $Cl^-$, $PF_6^-$, $Br^-$, $BF_4^-$, $ClO_4^-$, $CF_3SO_3^-$, and $SO_4^{-2}$;

n=0, 1, 2, 3, 4, or 5;

y=1, 2, or 3;

z=0, 1, or 2;

Lig at each occurrence is independently selected from the group consisting of

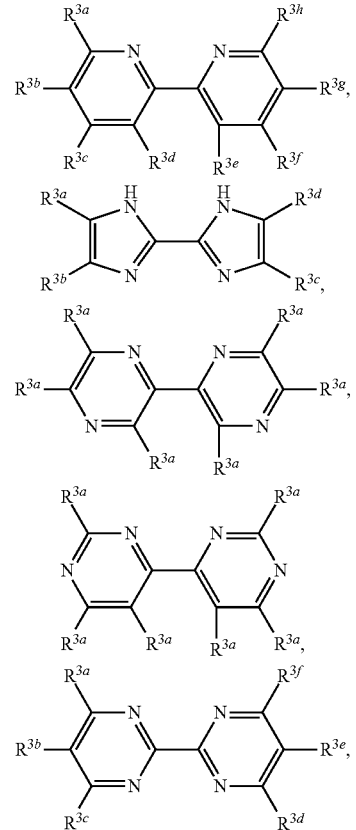

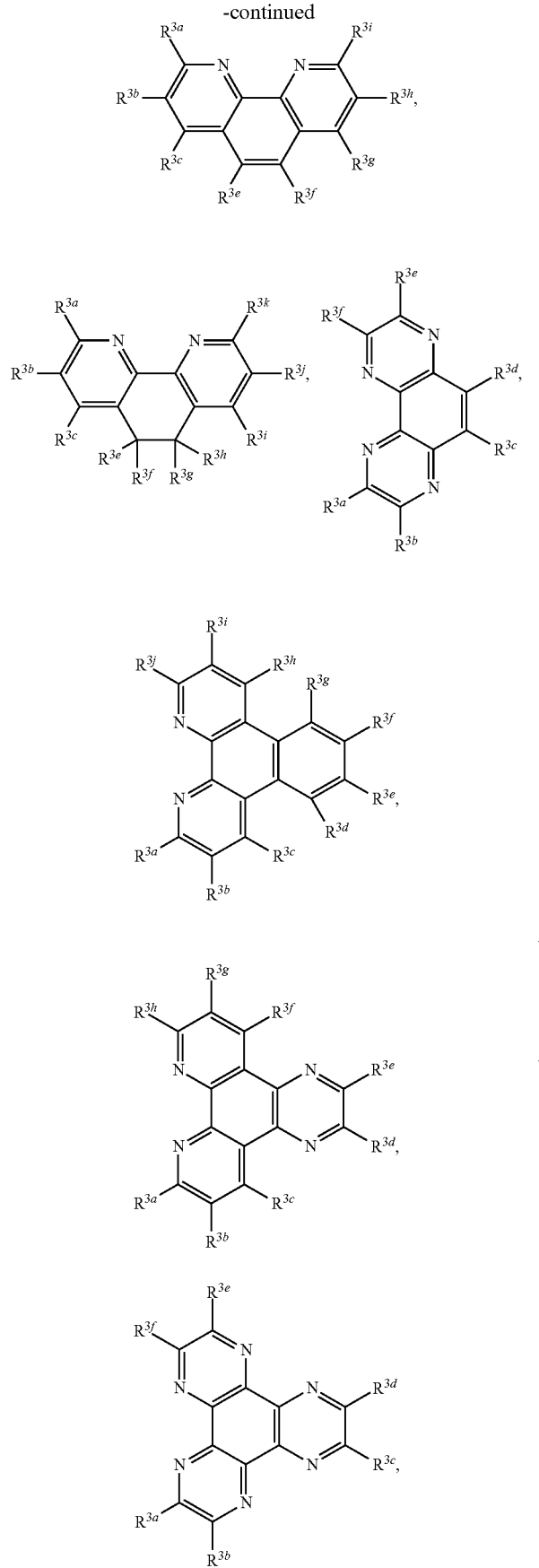
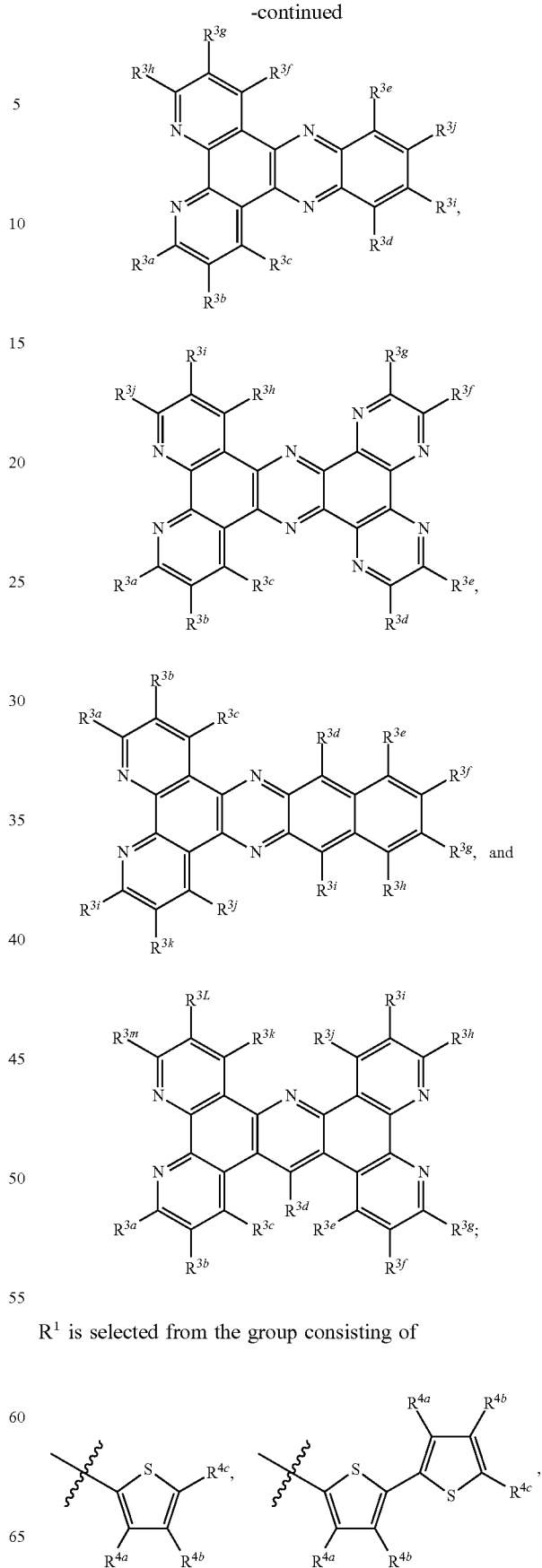
$R^1$ is selected from the group consisting of

-continued

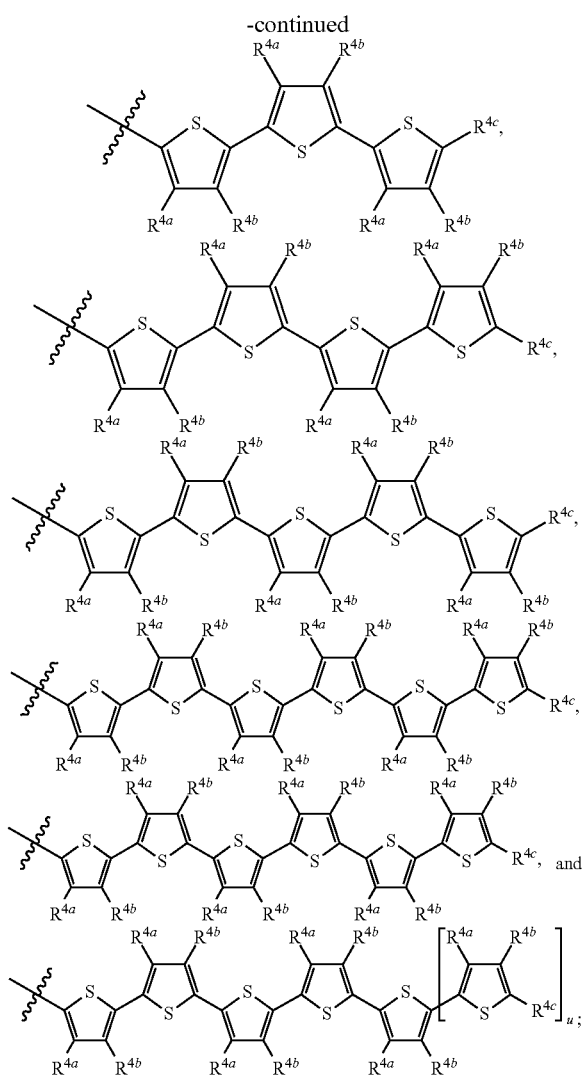

u is an integer;

$R^{2a}$, $R^{2b}$, $R^{2c}$, $R^{2d}$, $R^{2e}$, and $R^{2f}$ at each occurrence are each independently selected from the group consisting of hydrogen, C1-6 optionally substituted alkyl, C1-6 optionally substituted branched alkyl, C3-7 optionally substituted cycloalkyl, C1-6 optionally substituted haloalkyl, C1-6 optionally substituted alkoxy, $CO_2R^5$, $CONR^6_2$, $NR^7_2$, sulfate, sulfonate, optionally substituted aryl, optionally substituted aryloxy, optionally substituted heteroaryl, and optionally substituted heterocycle;

$R^{3a}$, $R^{3b}$, $R^{3c}$, $R^{3d}$, $R^{3e}$, $R^{3f}$, $R^{3g}$, $R^{3h}$, $R^{3i}$, $R^{3j}$, $R^{3k}$, $R^{3l}$, and $R^{3m}$ at each occurrence are each independently selected from the group consisting of hydrogen, C1-6 optionally substituted alkyl, C1-6 optionally substituted branched alkyl, C1-6 optionally substituted haloalkyl, C1-6 optionally substituted alkoxy, and $CO_2R^8$;

$R^{4a}$, $R^{4b}$, and $R^{4c}$ at each occurrence are each independently selected from the group consisting of hydrogen, C1-6 optionally substituted alkyl, C1-6 optionally substituted branched alkyl, C1-6 optionally substituted cycloalkyl, C1-6 optionally substituted haloalkyl, C1-6 optionally substituted alkoxy, $CO_2R^5$, $CONR^6_2$, $NR^7_2$, sulfate, sulfonate, optionally substituted aryl, optionally substituted aryloxy, optionally substituted heteroaryl, and optionally substituted heterocycle;

$R^{4a}$ and $R^{4b}$ at each occurrence on a thiophene ring are taken together with the atom to which they are bound to form an optionally substituted ring having from 6 ring atoms containing 2 oxygen atoms;

$R^5$ at each occurrence is independently selected from the group consisting of hydrogen and optionally substituted alkyl;

$R^6$ at each occurrence is independently selected from the group consisting of hydrogen and optionally substituted alkyl;

$R^7$ at each occurrence is independently selected from the group consisting of hydrogen and optionally substituted alkyl; and $R^8$ at each occurrence is independently selected from the group consisting of hydrogen and optionally substituted alkyl.

In certain embodiments, the photodynamic compound has a structure selected from the group consisting of:

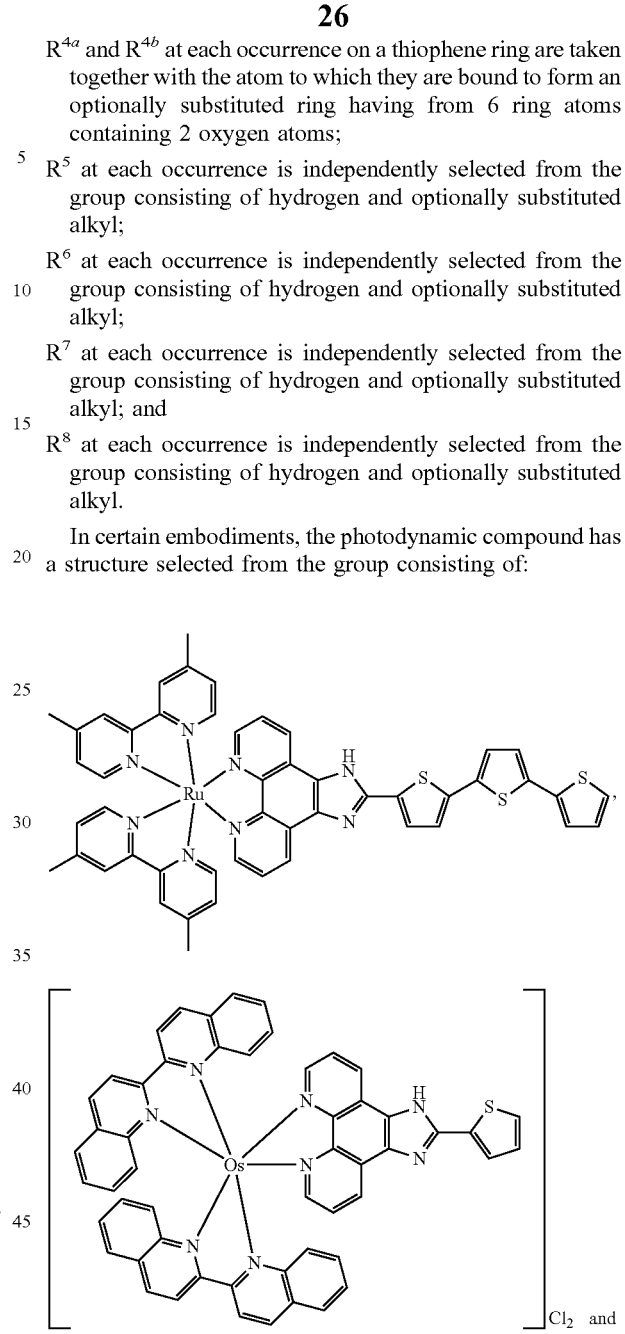

These and other objects, features, and advantages will become apparent to those of ordinary skill in the art from a reading of the following detailed description and the appended claims.

BRIEF DESCRIPTION OF SEVERAL VIEWS OF THE DRAWINGS

The invention will be described in conjunction with the following drawings, wherein.

DETAILED DESCRIPTION OF PREFERRED EMBODIMENTS OF THE INVENTION

Glossary

Figure 1:
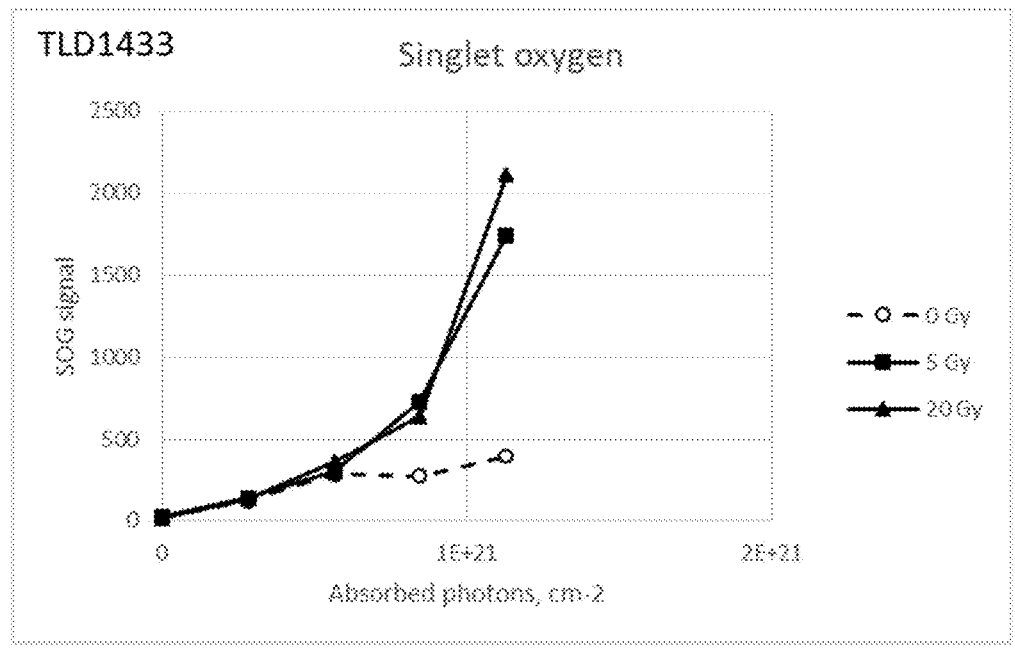
FIG. 1 shows a graph of Singlet Oxygen Green (SOG) fluorescence against photon absorption as a function of X-ray dosage for compound TLD1433.
Figure 2:
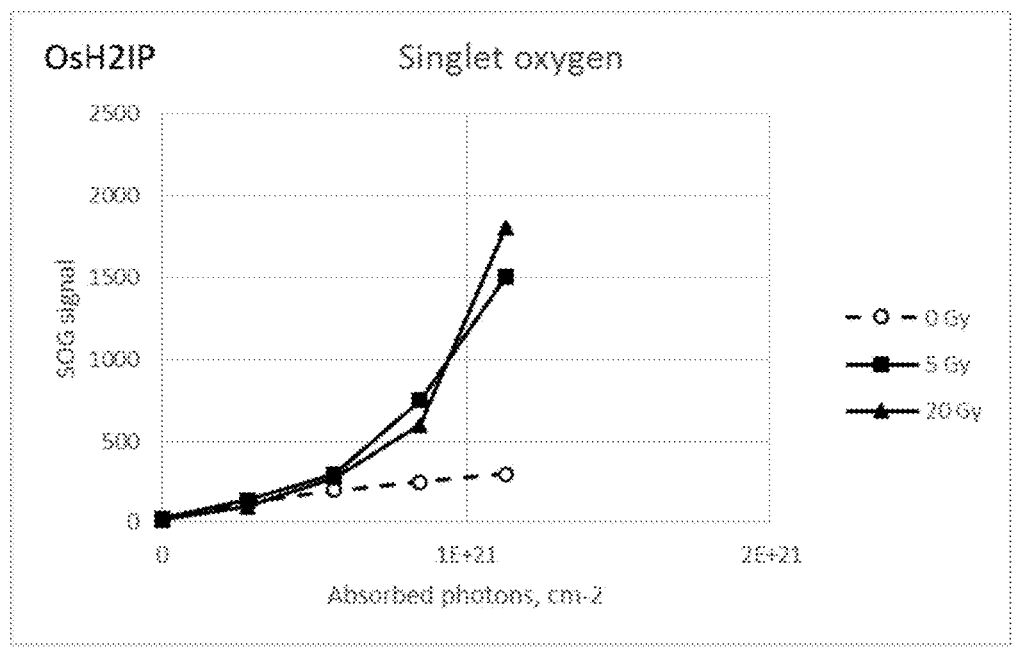
FIG. 2 shows a graph of SOG fluorescence against photon absorption as a function of X-ray dosage for compound OsH2IP.
Figure 3:
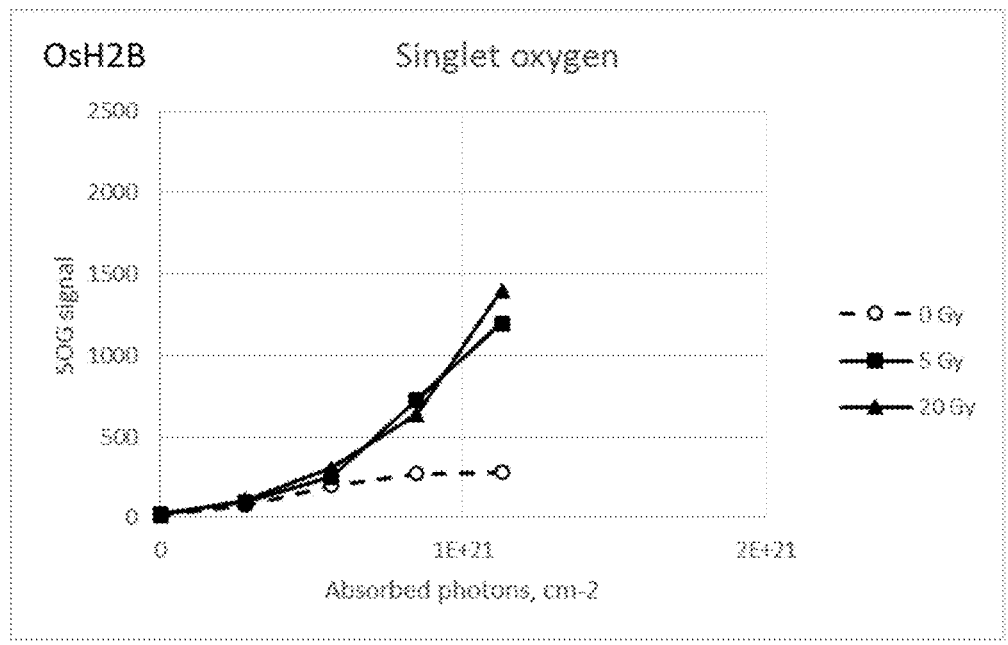
FIG. 3 shows a graph of SOG fluorescence against photon absorption as a function of X-ray dosage for compound OsH2B.
Figure 4:
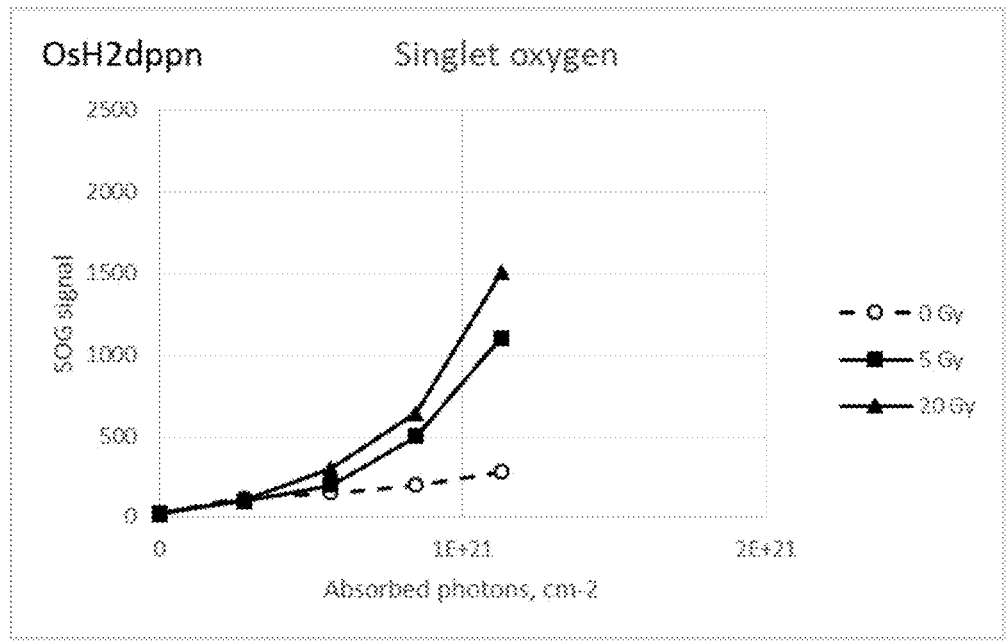
FIG. 4 shows a graph of SOG fluorescence against photon absorption as a function of X-ray dosage for compound OsH2dppn.
Figure 5A:
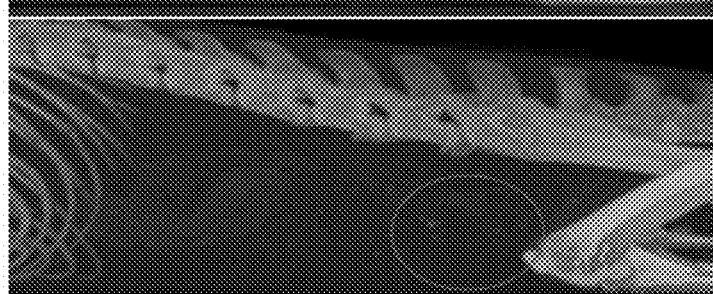
FIGS. 5A, 5B, 5C, 5D and 5E show CT images of rats following intravenous injection.
Figure 5B:
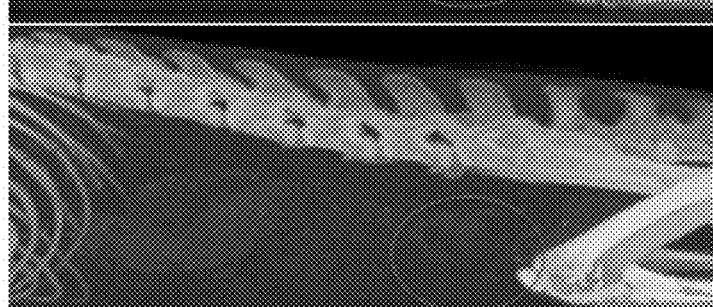
Figure 5C:
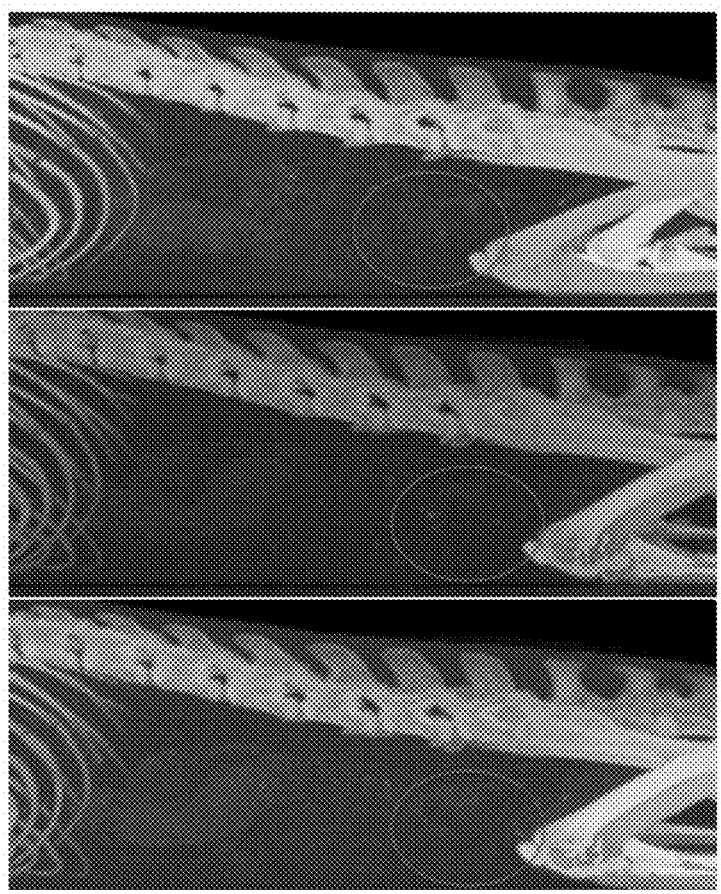
Figure 5D:
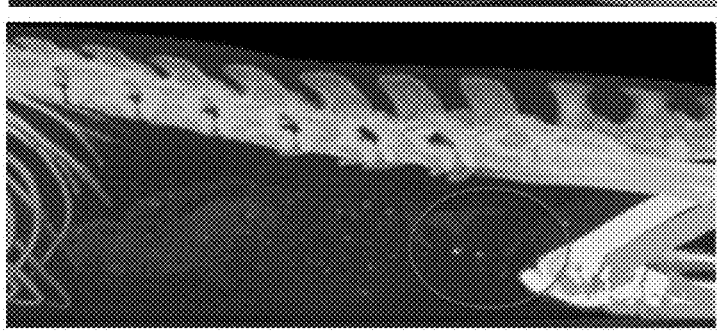
Figure 5E:
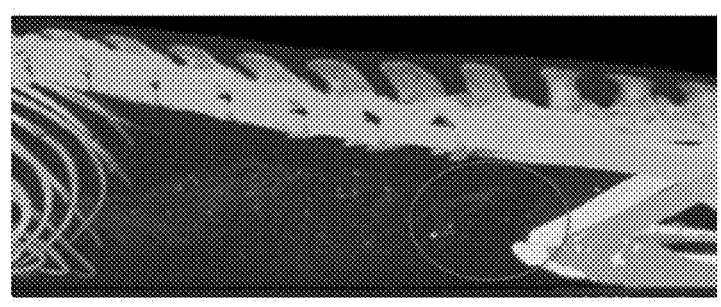

Throughout the description, where compositions are described as having, including, or comprising specific components, or where processes are described as having, including, or comprising specific process steps, it is contemplated that compositions of the present teachings also consist essentially of, or consist of, the recited components, and that the processes of the present teachings also consist essentially of, or consist of, the recited processing steps.

In the application, where an element or component is said to be included in and/or selected from a list of recited elements or components, it should be understood that the element or component can be any one of the recited elements or components and can be selected from a group consisting of two or more of the recited elements or components.

The use of the singular herein includes the plural (and vice versa) unless specifically stated otherwise. In addition, where the use of the term "about" is before a quantitative value, the present teachings also include the specific quantitative value itself, unless specifically stated otherwise.

It should be understood that the order of steps or order for performing certain actions is immaterial so long as the present teachings remain operable. Moreover, two or more steps or actions can be conducted simultaneously.

For the purposes of the present invention the terms "compound," "analog," and "composition of matter" stand equally well for the inventive compounds described herein, be they photodynamic or not, including all enantiomeric forms, diastereomeric forms, salts, and the like, and the terms "compound," "analog," and "composition of matter" are used interchangeably throughout the present specification.

Compounds described herein can contain an asymmetric atom (also referred as a chiral center), and some of the compounds can contain one or more asymmetric atoms or centers, which can thus give rise to optical isomers (enantiomers) and diastereomers. The present teachings and compounds disclosed herein include such enantiomers and diastereomers, as well as the racemic and resolved, enantiomerically pure R and S stereoisomers, as well as other mixtures of the R and S stereoisomers and pharmaceutically acceptable salts thereof. Optical isomers can be obtained in pure form by standard procedures known to those skilled in the art, which include, but are not limited to, diastereomeric salt formation, kinetic resolution, and asymmetric synthesis. The present teachings also encompass cis and trans isomers of compounds containing alkenyl moieties (e.g., alkenes and imines). It is also understood that the present teachings encompass all possible regioisomers, and mixtures thereof, which can be obtained in pure form by standard separation procedures known to those skilled in the art, and include, but are not limited to, column chromatography, thin-layer chromatography, and high-performance liquid chromatography.

Pharmaceutically acceptable salts of compounds of the present teachings, which can have an acidic moiety, can be formed using organic and inorganic bases. Both mono and polyanionic salts are contemplated, depending on the number of acidic hydrogens available for deprotonation. Suitable salts formed with bases include metal salts, such as alkali metal or alkaline earth metal salts, for example sodium, potassium, or magnesium salts; ammonia salts and organic amine salts, such as those formed with morpholine, thiomorpholine, piperidine, pyrrolidine, a mono-, di- or tri-lower alkylamine (e.g., ethyl-tert-butyl-, diethyl-, diisopropyl-, triethyl-, tributyl- or dimethylpropylamine), or a mono-, di-, or trihydroxy lower alkylamine (e.g., mono-, di- or triethanolamine). Specific non-limiting examples of inorganic bases include $NaHCO_3$, $Na_2CO_3$, $KHCO_3$, $K_2CO_3$, $Cs_2CO_3$, LiOH, NaOH, KOH, $NaH_2PO_4$, $Na_2HPO_4$, and $Na_3PO_4$. Internal salts also can be formed. Similarly, when a compound disclosed herein contains a basic moiety, salts can be formed using organic and inorganic acids. For example, salts can be formed from the following acids: acetic, propionic, lactic, benzenesulfonic, benzoic, camphorsulfonic, citric, tartaric, succinic, dichloroacetic, ethenesulfonic, formic, fumaric, gluconic, glutamic, hippuric, hydrobromic, hydrochloric, isethionic, lactic, maleic, malic, malonic, mandelic, methanesulfonic, mucic, naphthalenesulfonic, nitric, oxalic, pamoic, pantothenic, phosphoric, phthalic, propionic, succinic, sulfuric, tartaric, toluenesulfonic, and camphorsulfonic as well as other known pharmaceutically acceptable acids.

When any variable occurs more than one time in any constituent or in any formula, its definition in each occurrence is independent of its definition at every other occurrence (e.g., in $N(R^6)_2$, each $R^6$ may be the same or different than the other). Combinations of substituents and/or variables are permissible only if such combinations result in stable compounds.

The terms "treat" and "treating" and "treatment" as used herein, refer to partially or completely alleviating, inhibiting, ameliorating and/or relieving a condition from which a patient is suspected to suffer.

As used herein, "therapeutically effective" and "effective dose" refer to a substance or an amount that elicits a desirable biological activity or effect.

As used herein, the term "photodynamic therapy" refers to a treatment for destroying cells or modulating immune function, including immune response, of cells and tissue through use of a drug that can be activated by light of a certain wavelength and dose.

As used herein, the term "photodynamic compound" refers to a compound that provides photodynamic therapy.

Except when noted, the terms "subject" or "patient" are used interchangeably and refer to mammals such as human patients and non-human primates, as well as experimental animals such as rabbits, rats, and mice, and other animals.

Accordingly, the term "subject" or "patient" as used herein means any mammalian patient or subject to which the compounds of the invention can be administered. In an exemplary embodiment of the present invention, to identify subject patients for treatment according to the methods of the invention, accepted screening methods are employed to determine risk factors associated with a targeted or suspected disease or condition or to determine the status of an existing disease or condition in a subject. These screening methods include, for example, conventional work-ups to determine risk factors that may be associated with the targeted or suspected disease or condition. These and other routine methods allow the clinician to select patients in need of therapy using the methods and compounds of the present invention.

As used herein, the term "biological target" refers to an organ, tissue and/or cell of an organism and/or to the organism itself.

As used herein, the term "radiation" refers to electromagnetic radiation of any wavelength or waveband.

All percentages, ratios and proportions herein are by weight, unless otherwise specified. All temperatures are in degrees Celsius (° C.) unless otherwise specified. All documents cited are in relevant part, incorporated herein by reference; the citation of any document is not to be construed as an admission that it is prior art with respect to the present invention.

Method of the Invention

The method of the present invention is effective to: (a) inhibit proliferation of hyperproliferating cells in an organism; (b) destroy hyperproliferating cells in an organism; and/or (c) destroy targeted microorganisms in an organism or other medium.

Hyperproliferating cells are cells which have an abnormally high rate of cell division. Such cells include but are not limited to tumor or cancer cells (including but not limited to leukemia cells, ovarian cancer cells, Burkitt's lymphoma cells, breast cancer cells, gastric cancer cells, testicular cancer cells, melanoma cells and the like), and cells associated with psoriasis, warts, macular degeneration and other non-malignant hyperproliferating conditions. Thus, the method of the invention is useful for treating conditions associated with hyperproliferating cells, such as cancer, psoriasis, warts and/or macular degeneration.

Microorganisms targeted for destruction by the method of the invention include but are not limited to bacteria, viruses and fungi. Thus, embodiments of the inventive method are useful for disinfection, sterilization and/or treatment of conditions associated with bacterial, viral and/or fungal infection.

The method can be performed in vitro or in vivo. Biological targets of the invention are organisms, organs, tissues and/or cells amenable to treatment by the method of the invention. Organisms in which the method can be performed include but are not limited to warm-blooded and cold-blooded animals, particularly mammals, and most particularly humans.

The method of the invention comprises administering to the organism a composition comprising a photodynamic compound containing at least one transition metal. The mode of administration is not particularly limited. In certain embodiments, the composition can be adminstered by topical, oral, buccal, intravenous, intramuscular, intra-arterial, intramedullary, intrathecal, intraventricular, transdermal, subcutaneous, intraperitoneal, intranasal, enteral, sublingual, vaginal, ophthalmic, pulmonary or rectal routes.

After the photodynamic compound is adminstered to the organism, the compound is irradiated with electromagnetic radiation. In certain embodiments, radiation used for administering PDT includes, but is not limited to, gamma rays, X-rays, ultraviolet light, visible light, infrared light, microwaves and radio waves with X-rays, gamma rays, red light and infrared light being most preferred. The radiation wavelength or waveband is preferably selected to correspond with or at least overlap the wavelengths or wavebands that excite at least some of the photodynamic compounds present in the organism (or other medium). Photodynamic compounds typically have one or more absorption wavelengths or wavebands that excite them to produce the substances which damage or destroy target cells, tissues, organs, or tumors. Preferably, the radiation wavelength or waveband matches the excitation wavelength or waveband of the photodynamic compound and has low absorption by other cells, tissues and organs of the patient. In certain embodiments, radiation is adminstered in a first wavelength range from 600-925 nm and/or in a second wavelength range of 0.01-10 nm.

The dosage of radiation is preferably safe and effective to inhibit proliferation of hyperproliferating cells, destroy hyperproliferating cells and/or destroy targeted microorganisms. Factors relevant to determining a suitable dosage include the wavelength of the radiation, the depth of the target (e.g., cells, tissues, organs, anatomical sites, etc.) and other factors.

Administering ionizing radiation in the 1 keV-100 MeV range is preferred in certain embodiments. This not only covers the X-ray and a large part of gamma range but also involves energies (approximately 3 to 60 keV) impacting the charge transfer effect of the ruthenium and osmium based photosensitizers via photoelectric effect. To determine safety of the therapeutic radiation dose, a diagnostic dose for a chest pelvic CT scan (0.02 Sv) can be used. The Sv unit is related to biological effect of absorbed radiation (H) and is linked to the physically deposited dose (D) by a quality factor (Q): H=QD. Assuming Q≈1, the dose of 0.02 Sv is equivalent to ≈0.02 Gy; therefore, the therapeutic dose of 5 Gy is equivalent to ≈250 diagnostic CT scans or ≈2000 years of natural exposure (based on the average natural exposure of 0.0023 mSv in the US). Maximum therapeutic X-ray dose to patients is not defined and can be higher. For example, total radiotherapy local doses are usually in the range of 60-80 Gy for solid tumors; however, the dose should be delivered only concentrated on the tumor (using IMRT techniques) and never as a whole body irradiation. For example, whole body 5 Gy is in the range of the acute radiation poisoning syndrome (3-6 Gy) and is potentially highly lethal even with medical care.

In certain embodiments, the organism is irradiated with 0.1 to 100 Gy of X-ray radiation, which is effective to activate the photodynamic compound to inhibit proliferation of hyperproliferating cells and/or destroy cells in the organism. For example, it is contemplated that certain patients (e.g., pediatric patients) might be irradiated with only 5 milligray of X-ray radiation. Technology that significantly reduces the target irradiation area and scatter will enable X-ray dosages greater than 100 Gy.

The method is effective to inhibit proliferation of hyperproliferating cells, destroy hyperproliferating cells and/or destroy targeted microorganims. In certain embodiments, the efficacy of the method is established by increased cell kill percentage and/or reduced cell division relative to a control.

In preferred embodiments, the organism is irradiated with a combination of ionizing radiation (e.g., gamma rays and/or X-rays) and non-ionizing radiation radiation in an order and at a power which are synergistically effective to achieve at least one of the following results: (a) inhibiting proliferation of hyperproliferating cells in the organism; (b) destroying hyperproliferating cells in the organism; and (c) destroying targeted microorganisms in the organism. As shown in the Examples below, achieving a synergistic result may require the irradiation order to be ionizing radiation before non-ionizing radiation or non-ionizing radiation before ionizing radiation. (Compare, e.g., Benstead et al., "The effect of combined modality treatment with ionising radiation and TPPS-mediatedphotodynamic therapy on murine tail skin." Br J Cancer. 1990 July; 62(1):48-53.) In other embodiments, synergistic results are achieved regardless of the order of irradiation. Synergistic efficacy is established by showing that the cell kill percentage resulting from the combined application of radiation at a first wavelength and at a second wavelength is greater than the sum of the cell kill percentages resulting from the independent application of radiation at the first and second wavelengths.

Unlike WO 2015059379 A1, the method can be conducted in the absence of a molecular conjugate comprising a radioluminescent molecule and a photosensitizer.

Photodynamic compounds suitable for use in the invention can be prepared in accordance with the procedures outlined herein, from commercially available starting materials, compounds known in the literature, or readily prepared intermediates, by employing standard synthetic methods and procedures known to those skilled in the art.

Suitable photodynamic compounds include but are not limited to compounds disclosed in WO 2013158550 A1, WO 2014145428 A2, U.S. Pat. Nos. 6,962,910, 7,612,057, 8,445,475 or 8,148,360. Other photodynamic compounds suitable for use in the invention include but are not limited to RAPTA, NAMI, KP1019 and analogs thereof.

Suitable photodynamic compounds preferably contain at least one transition metal, which is preferably a Group 8 or 9 metal, such as Fe, Ru, Os, Co, Rh and Ir, and is most preferably at least one of Ru, Rh and Os.

In certain embodiments, the photodynamic compounds comprise transitional metal-based combinations that are optionally surrounded (directly and/or indirectly binded) by various ligands, such as in coordination compounds. In some of these embodiments, bridging ligands are included, which are highly electron donating to the metal(s).

In certain embodiments, the photodynamic compound has the formula (I):

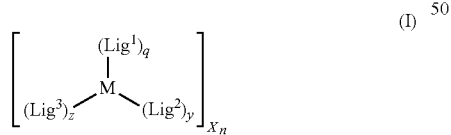

(I)

including hydrates, solvates, pharmaceutically acceptable salts, prodrugs and complexes thereof, wherein:
M at each occurrence is independently a transition metal, which is preferably selected from the group consisting of osmium, ruthenium and rhodium;
X is selected from the group consisting of $Cl^-$, $PF_6^-$, $Br^-$, $BF_4^-$, $ClO_4^-$, $CF_3SO_3^-$, and $SO_4^{-2}$;
n=0, 1, 2, 3, 4, or 5;
q is independently at each occurrence 0, 1, or 2;
y is independently at each occurrence 0, 1, or 2;
z is independently at each occurrence 1, 2, or 3;

$Lig^1$ is a bidentate ligand that at each occurrence is each independently selected from the group consisting of

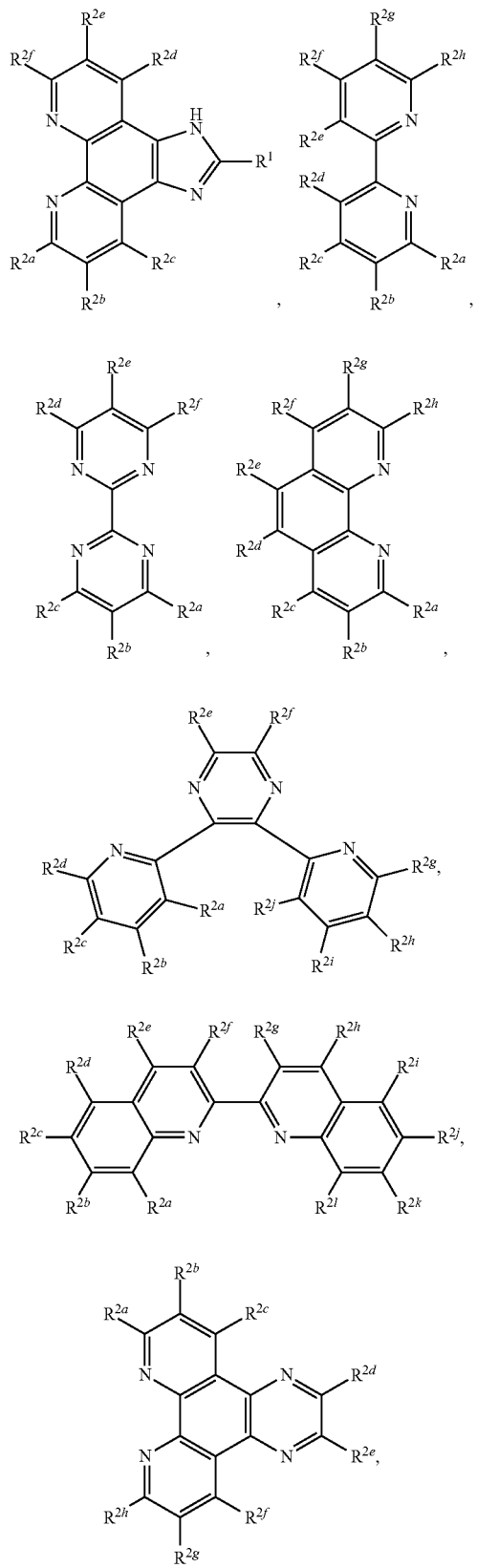

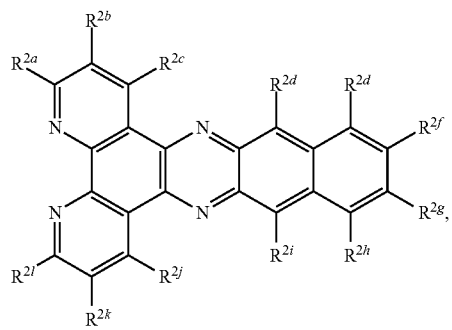
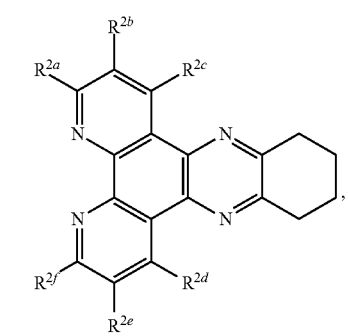
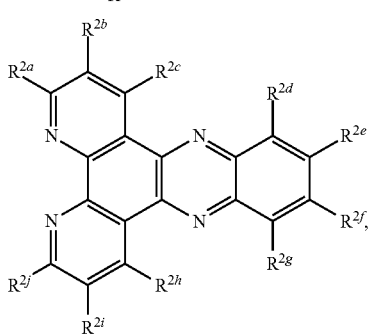
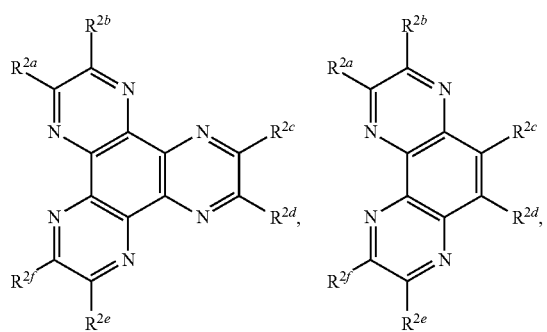
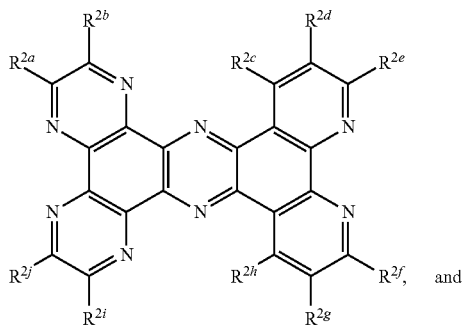
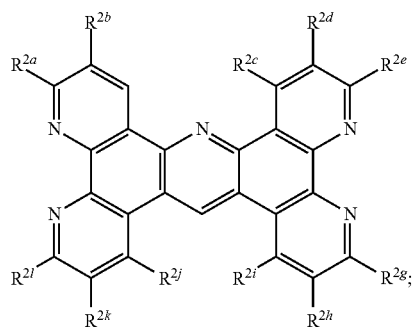
Lig² is a bidentate ligand that at each occurrence is each independently selected from the group consisting of
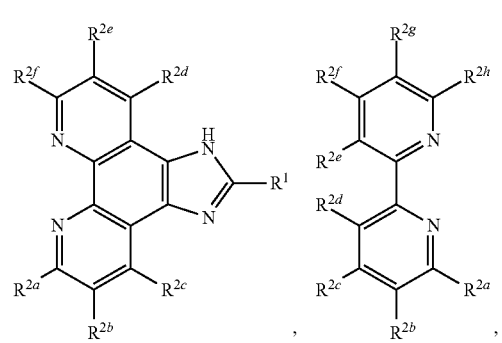
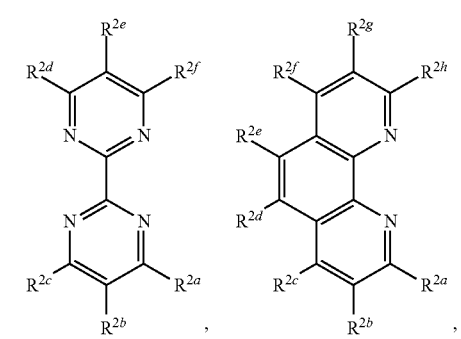
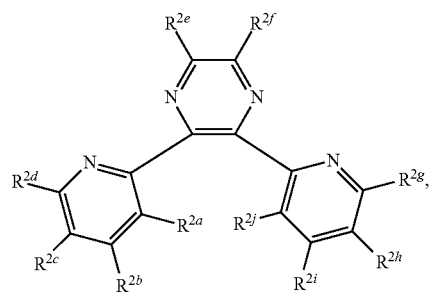
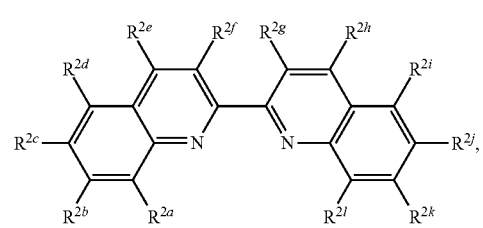

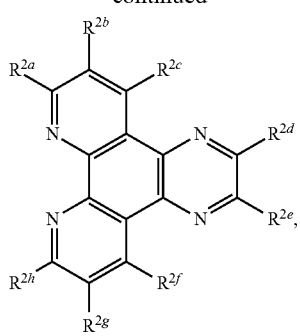
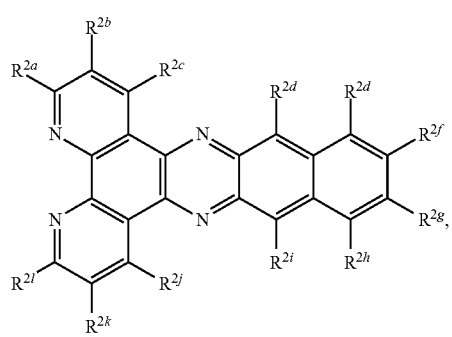
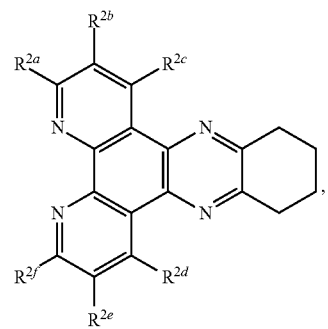
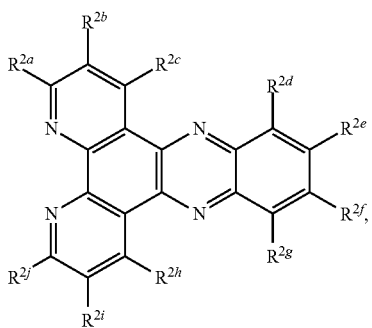
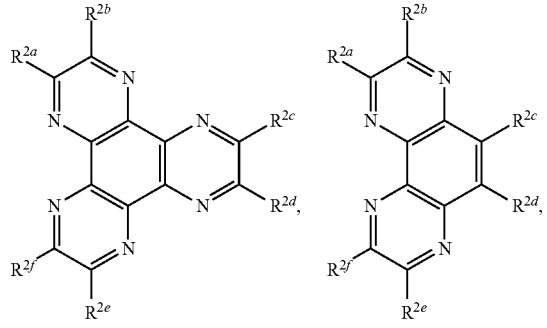
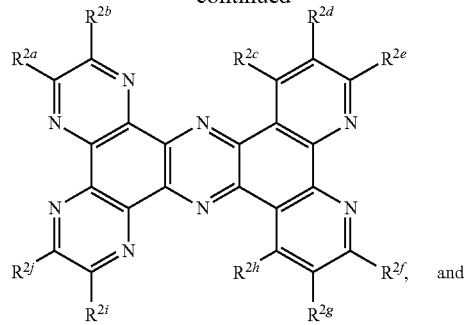
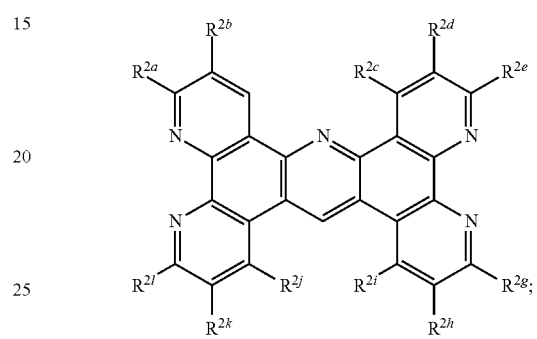
Lig³ is a bidentate ligand that at each occurrence is each independently selected from the group consisting of
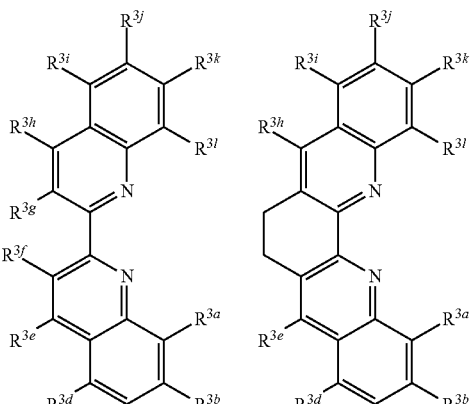
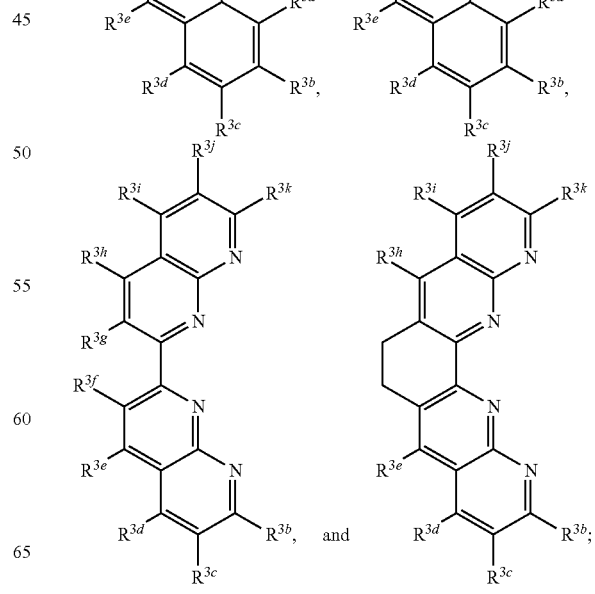

R[1] is selected from the group consisting of hydrogen, optionally substituted phenyl, optionally substituted aryl, optionally substituted heteroaryl, 4-pyridyl, 3-pyridyl, 2-thiazole, 2-pyrolyl, 2-furanyl,

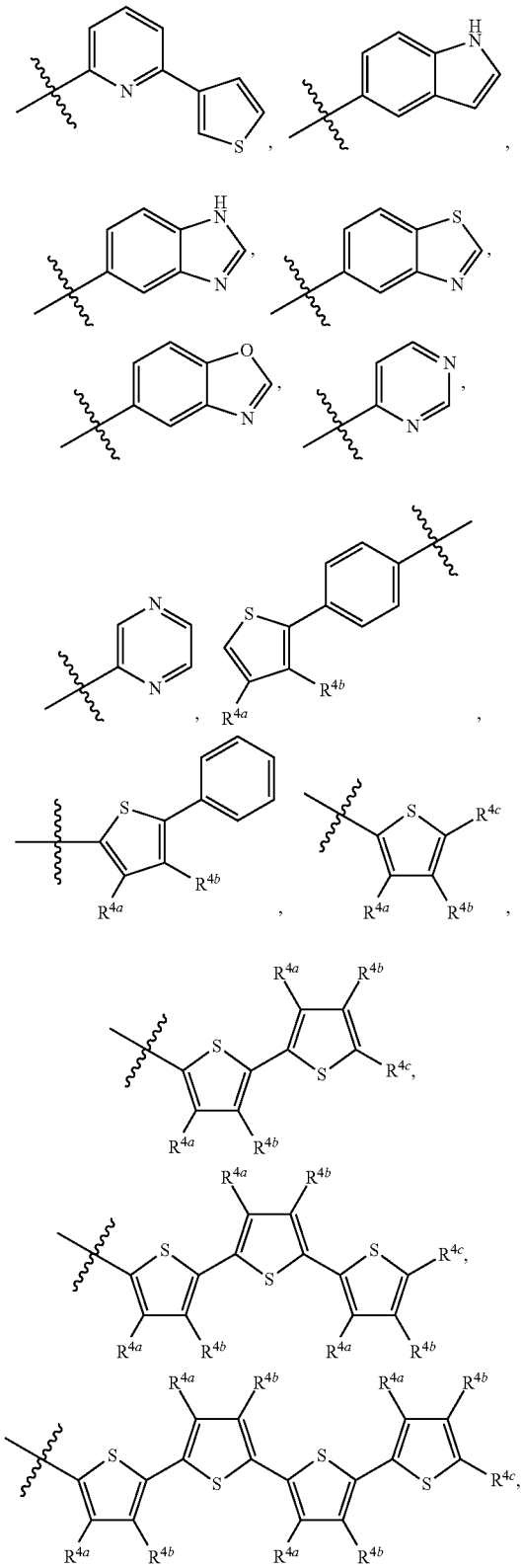

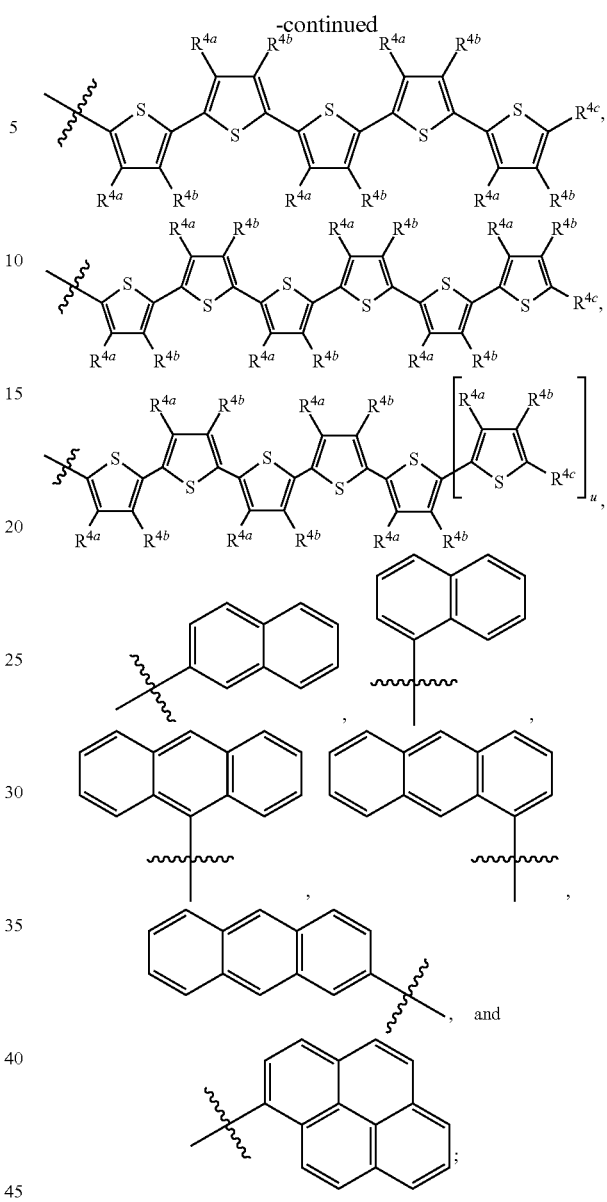

u is an integer;
$R^{2a}$, $R^{2b}$, $R^{2c}$, $R^{2d}$, $R^{2e}$, $R^{2f}$, $R^{2g}$, $R^{2h}$, $R^{2i}$, $R^{2j}$, $R^{2k}$, and $R^{2l}$ at each occurrence are each independently selected from the group consisting of hydrogen, $C_{1-6}$ optionally substituted alkyl, $C_{1-6}$ optionally substituted branched alkyl, $C_{3-7}$ optionally substituted cycloalkyl, $C_{1-6}$ optionally substituted haloalkyl, $C_{1-6}$ optionally substituted alkoxy, $CO_2R^5$, $CONR^6_2$, $NR^7_2$, $SO_3H$, sulfate, sulfonate, optionally substituted aryl, optionally substituted aryloxy, optionally substituted heteroaryl, and optionally substituted heterocycle;
$R^{3a}$, $R^{3b}$, $R^{3c}$, $R^{3d}$, $R^{3e}$, $R^{3f}$, $R^{3g}$, $R^{3h}$, $R^{3i}$, $R^{3j}$, $R^{3k}$, and $R^{3l}$ at each occurrence are each independently selected from the group consisting of hydrogen, $C_{1-6}$ optionally substituted alkyl, $C_{1-6}$ optionally substituted branched alkyl, $C_{1-6}$ optionally substituted haloalkyl, $C_{1-6}$ optionally substituted alkoxy, optionally substituted phenyl, and $CO_2R^8$;
$R^{4a}$, $R^{4b}$, and $R^{4c}$ at each occurrence are each independently selected from the group consisting of hydrogen, $C_{1-6}$ optionally substituted alkyl, $C_{1-6}$ optionally substituted branched alkyl, $C_{1-6}$ optionally substituted cycloalkyl, $C_{1-6}$ optionally substituted haloalkyl, $C_{1-6}$ optionally substituted alkoxy, $CO_2R^5$, $CONR^6{}_2$, $NR^7{}_2$, sulfate, sulfonate, optionally substituted aryl, optionally substituted aryloxy, optionally substituted heteroaryl, and optionally substituted heterocycle;

$R^{4a}$ and $R^{4b}$ at each occurrence on a thiophene ring are taken together with the atom to which they are bound to form an optionally substituted ring having from 6 ring atoms containing 2 oxygen atoms;

$R^5$ at each occurrence are each independently selected from the group consisting of hydrogen and optionally substituted alkyl;

$R^6$ at each occurrence are each independently selected from the group consisting of hydrogen and optionally substituted alkyl;

$R^7$ at each occurrence are each independently selected from the group consisting of hydrogen and optionally substituted alkyl; and $R^8$ at each occurrence are each independently selected from the group consisting of hydrogen and optionally substituted alkyl.

In certain embodiments, the photodynamic compound has the formula (VI):

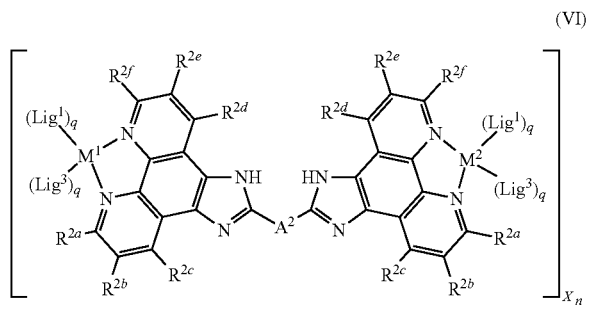

(VI)

including hydrates, solvates, pharmaceutically acceptable salts, prodrugs and complexes thereof wherein;

$M^1$ and $M^2$ at each occurrence is independently a transition metal, and is preferably independently selected from the group consisting of osmium, manganese, molybdenum, rhenium, ruthenium, iron, cobalt, rhodium, iridium, nickel, platinum, and copper;

$A^2$ is selected from the group consisting of

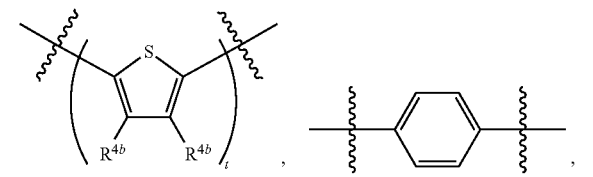

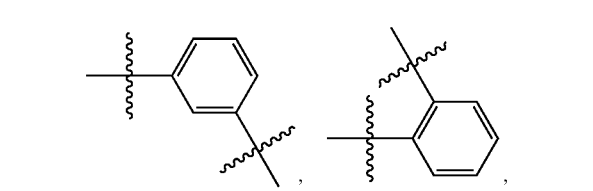

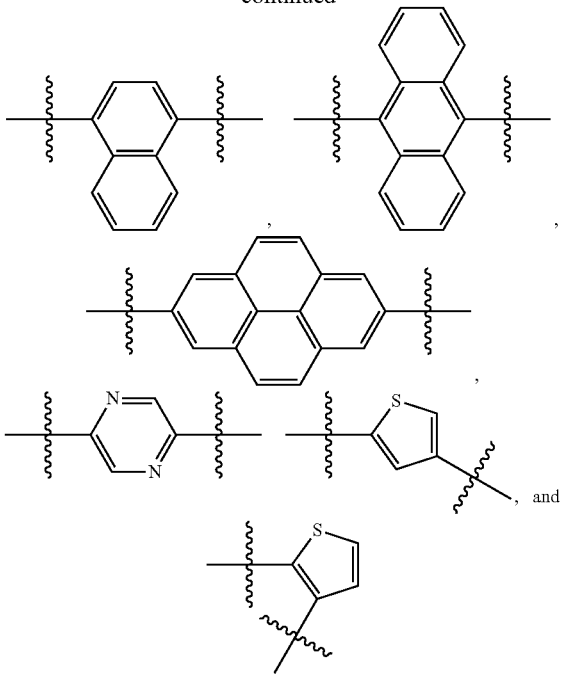

$t$ is an integer.

In certain embodiments, the photodynamic compound has the formula (VIIa)

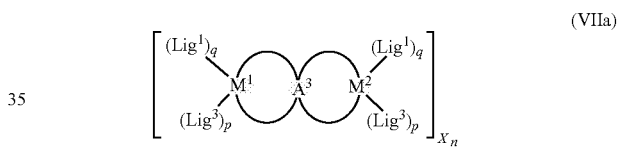

(VIIa)

including hydrates, solvates, pharmaceutically acceptable salts, prodrugs and complexes thereof wherein:

$M^1$ and $M^2$ at each occurrence is independently a transition metal, and is preferably independently selected from the group consisting of osmium, manganese, molybdenum, rhenium, ruthenium, iron, cobalt, rhodium, iridium, nickel, platinum, and copper;

$Lig^1$ is a bidentate ligand that at each occurrence is each independently selected from the group defined above;

$Lig^3$ is a bidentate ligand that at each occurrence is each independently selected from the group defined above;

$p$ is independently at each occurrence 0, 1, or 2;

$q$ is independently at each occurrence 0, 1, or 2;

$n$ is 0, 1, 2, 3, 4, or 5; and $A^3$ is selected from the group consisting of

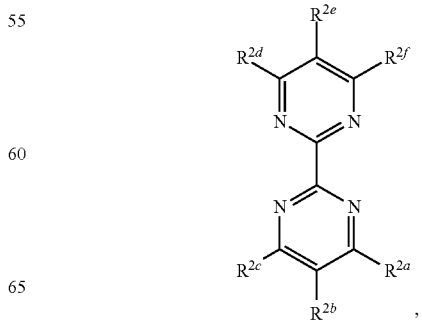

-continued

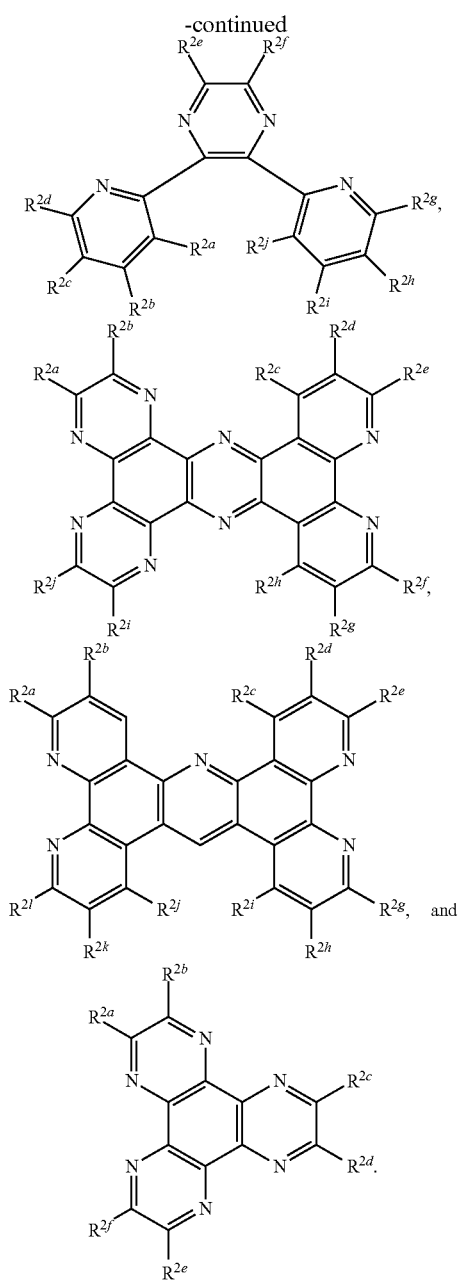

In certain embodiments, the photodynamic compound has the formula (II)

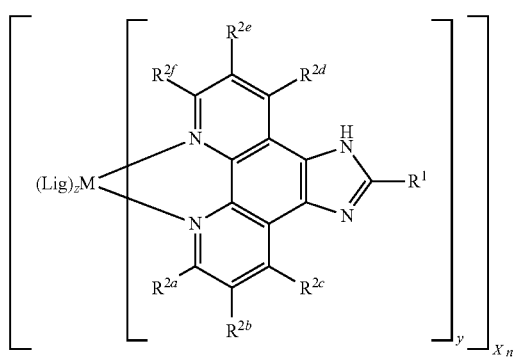

including hydrates, solvates, pharmaceutically acceptable salts, prodrugs and complexes thereof, wherein:

M is a transition metal preferably selected from the group consisting of manganese, molybdenum, rhenium, iron, ruthenium, osmium, cobalt, rhodium, iridium, nickel, platinum, and copper;

X is selected from the group consisting of $Cl^-$, $PF_6^-$, $Br^-$, $BF_4^-$, $ClO_4^-$, $CF_3SO_3^-$, and $SO_4^{-2}$;

n=0, 1, 2, 3, 4, or 5;

y=1, 2, or 3;

z=0, 1, or 2;

Lig at each occurrence is independently selected from the group consisting of

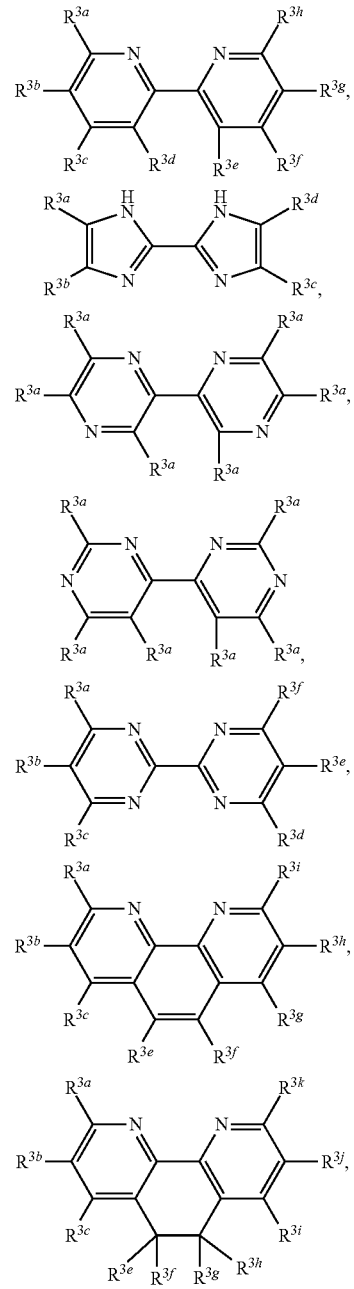

-continued
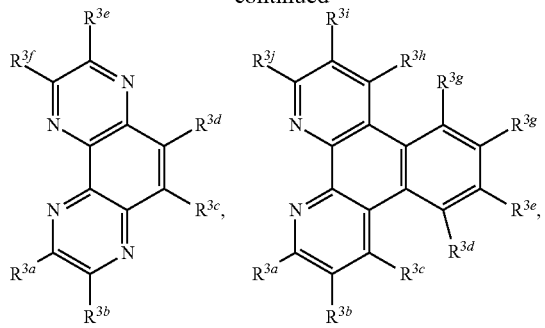
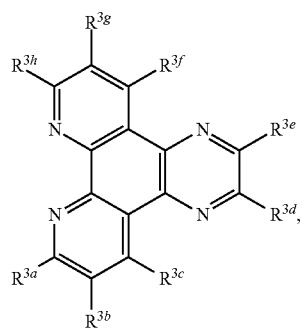
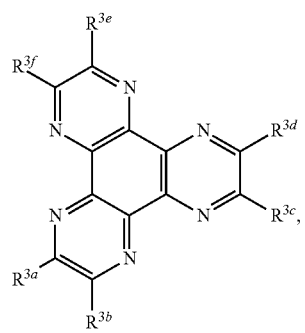
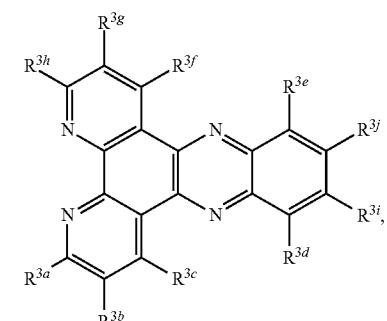
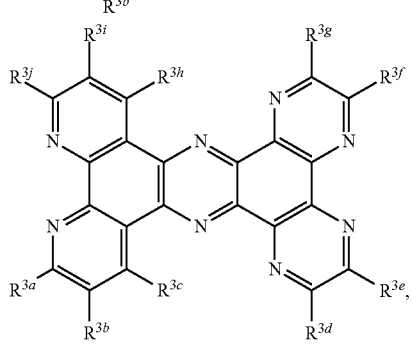
-continued
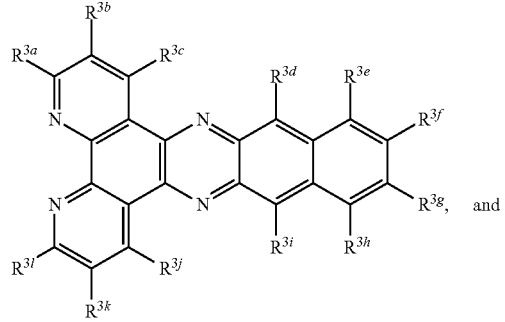
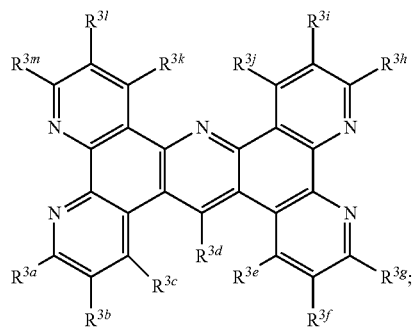
$R^1$ is selected from the group consisting of
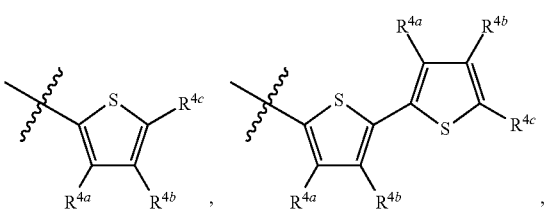
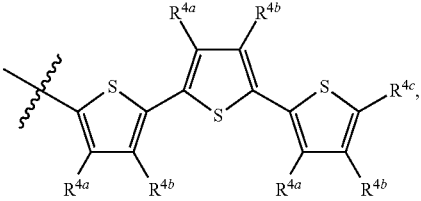
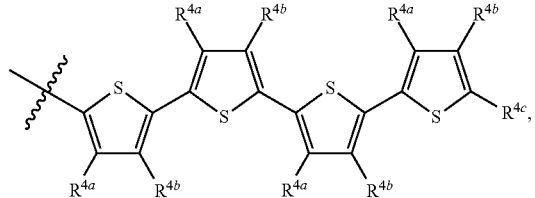
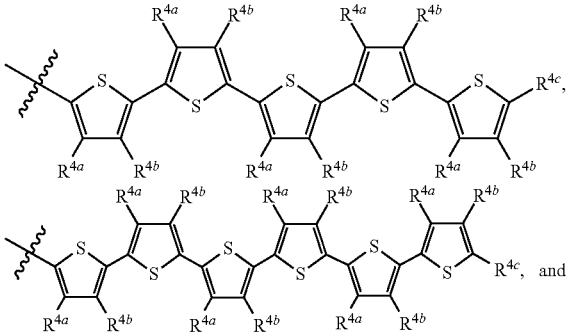

-continued

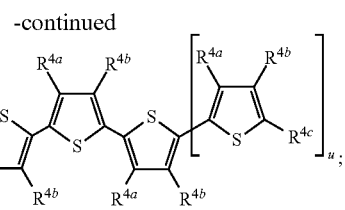

u is an integer;

$R^{1a}$, $R^{2b}$, $R^{2c}$, $R^{2d}$, $R^{2e}$, and $R^{2f}$ at each occurrence are each independently selected from the group consisting of hydrogen, C1-6 optionally substituted alkyl, C1-6 optionally substituted branched alkyl, C3-7 optionally substituted cycloalkyl, C1-6 optionally substituted haloalkyl, C1-6 optionally substituted alkoxy, $CO_2R^5$, $CONR^6{}_2$, $NR^7{}_2$, sulfate, sulfonate, optionally substituted aryl, optionally substituted aryloxy, optionally substituted heteroaryl, and optionally substituted heterocycle;

$R^{3a}$, $R^{3b}$, $R^{3c}$, $R^{3d}$, $R^{3e}$, $R^{3f}$, $R^{3g}$, $R^{3h}$, $R^{3i}$, $R^{3j}$, $R^{3k}$, $R^{3l}$, and $R^{3m}$ at each occurrence are each independently selected from the group consisting of hydrogen, C1-6 optionally substituted alkyl, C1-6 optionally substituted branched alkyl, C1-6 optionally substituted haloalkyl, C1-6 optionally substituted alkoxy, and $CO_2R^8$;

$R^{4a}$, $R^{4b}$, and $R^{4c}$ at each occurrence are each independently selected from the group consisting of hydrogen, C1-6 optionally substituted alkyl, C1-6 optionally substituted branched alkyl, C1-6 optionally substituted cycloalkyl, C1-6 optionally substituted haloalkyl, C1-6 optionally substituted alkoxy, $CO_2R^5$, $CONR^6{}_2$, $NR^7{}_2$, sulfate, sulfonate, optionally substituted aryl, optionally substituted aryloxy, optionally substituted heteroaryl, and optionally substituted heterocycle;

$R^{4a}$ and $R^{4b}$ at each occurrence on a thiophene ring are taken together with the atom to which they are bound to form an optionally substituted ring having from 6 ring atoms containing 2 oxygen atoms;

$R^5$ at each occurrence is independently selected from the group consisting of hydrogen and optionally substituted alkyl;

$R^6$ at each occurrence is independently selected from the group consisting of hydrogen and optionally substituted alkyl;

$R^7$ at each occurrence is independently selected from the group consisting of hydrogen and optionally substituted alkyl; and $R^8$ at each occurrence is independently selected from the group consisting of hydrogen and optionally substituted alkyl.

In all of the embodiments provided herein, examples of suitable optional substituents are not intended to limit the scope of the claimed invention. The photodynamic compounds may contain any of the substituents, or combinations of substituents, provided herein.

Preferred embodiments of the invention comprise an effective amount of at least one photodynamic compound to inhibit proliferation of hyperproliferating cells, and at least one excipient or carrier. For the purposes of the present invention the term "excipient" and "carrier" are used interchangeably throughout the description of the present invention and said terms are defined herein as, "ingredients which are used in the practice of formulating a safe and effective pharmaceutical composition."

The formulator will understand that excipients are used primarily to serve in delivering a safe, stable, and functional pharmaceutical, serving not only as part of the overall vehicle for delivery but also as a means for achieving effective absorption by the recipient of the active ingredient. An excipient may fill a role as simple and direct as being an inert filler, or an excipient as used herein may be part of a pH stabilizing system or coating to insure delivery of the ingredients safely to the stomach. The formulator can also take advantage of the fact the compounds of the present invention have improved cellular potency, pharmacokinetic properties, as well as improved oral bioavailability.

Suitable carriers are well known to those skilled in the art and can be prepared in accordance with acceptable pharmaceutical procedures, such as, for example, those described in Remington's Pharmaceutical Sciences, 17th edition, ed. Alfonoso R. Gennaro, Mack Publishing Company, Easton, Pa. (1985), the entire disclosure of which is incorporated by reference herein for all purposes. As used herein, "pharmaceutically acceptable" refers to a substance that is acceptable for use in pharmaceutical applications from a toxicological perspective and does not adversely interact with the active ingredient. Accordingly, pharmaceutically acceptable carriers are those that are compatible with the other ingredients in the formulation and are biologically acceptable. Supplementary active ingredients can also be incorporated into the pharmaceutical compositions.

In preferred embodiments, photodynamic compound containing compositions further comprise a metal-binding glycoprotein (preferably transferrin) as a delivery vehicle for metal-based photodynamic compounds, so as to facilitate delivery of the photodynamic compounds into a biological target. Non-limiting examples of such compositions, which are suitable for use in the inventive method, are disclosed in PCT/IB2016/050253.

In certain embodiments, a combination of different transitional metal photodynamic compounds can be used. At least one, more than one or all of the different photodynamic compounds are preferably excitable by ionizing radiation. Photodynamic compounds in the combination that are not excitable by ionizing radiation can be excited by energy transfer from activated photodynamic compounds.

Photodynamic compounds can be administered orally or parenterally, neat or in combination with conventional pharmaceutical carriers. Applicable solid carriers can include one or more substances which can also act as flavoring agents, lubricants, solubilizers, suspending agents, fillers, glidants, compression aids, binders or tablet-disintegrating agents, or encapsulating materials. The compounds can be formulated in conventional manner, for example, in a manner similar to that used for known neuroprotective agents. Oral formulations containing a compound disclosed herein can comprise any conventionally used oral form, including tablets, capsules, buccal forms, troches, lozenges and oral liquids, suspensions or solutions. In powders, the carrier can be a finely divided solid, which is an admixture with a finely divided compound. In tablets, a compound disclosed herein can be mixed with a carrier having the necessary compression properties in suitable proportions and compacted in the shape and size desired. The powders and tablets can contain up to 99% of the compound.

Capsules can contain mixtures of one or more compound(s) disclosed herein with inert filler(s) and/or diluent(s) such as pharmaceutically acceptable starches (e.g., corn, potato or tapioca starch), sugars, artificial sweetening agents, powdered celluloses (e.g., crystalline and microcrystalline celluloses), flours, gelatins, gums, and the like.

Useful tablet formulations can be made by conventional compression, wet granulation or dry granulation methods and utilize pharmaceutically acceptable diluents, binding agents, lubricants, disintegrants, surface modifying agents (including surfactants), suspending or stabilizing agents, including, but not limited to, magnesium stearate, stearic acid, sodium lauryl sulfate, talc, sugars, lactose, dextrin, starch, gelatin, cellulose, methyl cellulose, microcrystalline cellulose, sodium carboxymethyl cellulose, carboxymethylcellulose calcium, polyvinylpyrrolidine, alginic acid, acacia gum, xanthan gum, sodium citrate, complex silicates, calcium carbonate, glycine, sucrose, sorbitol, dicalcium phosphate, calcium sulfate, lactose, kaolin, mannitol, sodium chloride, low melting waxes, and ion exchange resins. Surface modifying agents include nonionic and anionic surface modifying agents. Representative examples of surface modifying agents include, but are not limited to, poloxamer 188, benzalkonium chloride, calcium stearate, cetostearl alcohol, cetomacrogol emulsifying wax, sorbitan esters, colloidal silicon dioxide, phosphates, sodium dodecylsulfate, magnesium aluminum silicate, and triethanolamine. Oral formulations herein can utilize standard delay or time-release formulations to alter the absorption of the compound(s). The oral formulation can also consist of administering a compound disclosed herein in water or fruit juice, containing appropriate solubilizers or emulsifiers as needed.

Liquid carriers can be used in preparing solutions, suspensions, emulsions, syrups, elixirs, and for inhaled delivery. A compound of the present teachings can be dissolved or suspended in a pharmaceutically acceptable liquid carrier such as water, an organic solvent, or a mixture of both, or a pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers, and osmo-regulators. Examples of liquid carriers for oral and parenteral administration include, but are not limited to, water (particularly containing additives as described herein, e.g., cellulose derivatives such as a sodium carboxymethyl cellulose solution), alcohols (including monohydric alcohols and polyhydric alcohols, e.g., glycols) and their derivatives, and oils (e.g., fractionated coconut oil and arachis oil). For parenteral administration, the carrier can be an oily ester such as ethyl oleate and isopropyl myristate. Sterile liquid carriers are used in sterile liquid form compositions for parenteral administration. The liquid carrier for pressurized compositions can be halogenated hydrocarbon or other pharmaceutically acceptable propellants.

Liquid pharmaceutical compositions, which are sterile solutions or suspensions, can be utilized by, for example, intramuscular, intraperitoneal or subcutaneous injection. Sterile solutions can also be administered intravenously. Compositions for oral administration can be in either liquid or solid form.

Preferably the pharmaceutical composition is in unit dosage form, for example, as tablets, capsules, powders, solutions, suspensions, emulsions, granules, or suppositories. In such form, the pharmaceutical composition can be sub-divided in unit dose(s) containing appropriate quantities of the compound. The unit dosage forms can be packaged compositions, for example, packeted powders, vials, ampoules, prefilled syringes or sachets containing liquids. Alternatively, the unit dosage form can be a capsule or tablet itself, or it can be the appropriate number of any such compositions in package form. Such unit dosage form can contain from 0.0001 or 0.001 or 0.01 or 0.1 or 1 or 10 or 100 mg/kg of compound to 0.0005 or 0.005 or 0.05 or 0.5 or 5 or 50 or 500 mg/kg of compound, and can be given in a single dose or in two or more doses. Such doses can be administered in any manner useful in directing the compound(s) to the recipient's bloodstream, including orally, via implants, parenterally (including intravenous, intraperitoneal and subcutaneous injections), rectally, vaginally, and transdermally.

When administered for the treatment or inhibition of a particular disease state or disorder, it is understood that an effective dosage can vary depending upon the particular compound utilized, the mode of administration, and severity of the condition being treated, as well as the various physical factors related to the individual being treated. In therapeutic applications, a compound of the present teachings can be provided to a patient already suffering from a disease in an amount sufficient to cure or at least partially ameliorate the symptoms of the disease and its complications. The dosage to be used in the treatment of a specific individual typically must be subjectively determined by the attending physician. The variables involved include the specific condition and its state as well as the size, age and response pattern of the patient.

In some cases it may be desirable to administer a compound directly to the airways of the patient, using devices such as, but not limited to, metered dose inhalers, breath-operated inhalers, multidose dry-powder inhalers, pumps, squeeze-actuated nebulized spray dispensers, aerosol dispensers, and aerosol nebulizers. For administration by intranasal or intrabronchial inhalation, the photodynamic compound can be formulated into a liquid composition, a solid composition, or an aerosol composition. The liquid composition can include, by way of illustration, one or more photodynamic compounds dissolved, partially dissolved, or suspended in one or more pharmaceutically acceptable solvents and can be administered by, for example, a pump or a squeeze-actuated nebulized spray dispenser. The solvents can be, for example, isotonic saline or bacteriostatic water. The solid composition can be, by way of illustration, a powder preparation including one or more compounds of the present teachings intermixed with lactose or other inert powders that are acceptable for intrabronchial use, and can be administered by, for example, an aerosol dispenser or a device that breaks or punctures a capsule encasing the solid composition and delivers the solid composition for inhalation. The aerosol composition can include, by way of illustration, one or more compounds of the present teachings, propellants, surfactants, and co-solvents, and can be administered by, for example, a metered device. The propellants can be a chlorofluorocarbon (CFC), a hydrofluoroalkane (HFA), or other propellants that are physiologically and environmentally acceptable.

Photodynamic compounds described herein can be administered parenterally or intraperitoneally. Solutions or suspensions of these compounds or a pharmaceutically acceptable salts, hydrates, or esters thereof can be prepared in water suitably mixed with a surfactant such as hydroxylpropylcellulose. Dispersions can also be prepared in glycerol, liquid polyethylene glycols, and mixtures thereof in oils. Under ordinary conditions of storage and use, these preparations typically contain a preservative to inhibit the growth of microorganisms.

The pharmaceutical forms suitable for injection can include sterile aqueous solutions or dispersions and sterile powders for the extemporaneous preparation of sterile injectable solutions or dispersions. In some embodiments, the form can sterile and its viscosity permits it to flow through a syringe. The form preferably is stable under the conditions of manufacture and storage and can be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

Photodynamic compounds described herein can be administered transdermally, i.e., administered across the surface of the body and the inner linings of bodily passages including epithelial and mucosal tissues. Such administration can be carried out using the compounds of the present teachings including pharmaceutically acceptable salts, hydrates, or esters thereof, in lotions, creams, foams, patches, suspensions, solutions, and suppositories (rectal and vaginal).

Transdermal administration can be accomplished through the use of a transdermal patch containing a photodynamic compound and a carrier that can be inert to the compound, can be non-toxic to the skin, and can allow delivery of the compound for systemic absorption into the blood stream via the skin. The carrier can take any number of forms such as creams and ointments, pastes, gels, and occlusive devices. The creams and ointments can be viscous liquid or semisolid emulsions of either the oil-in-water or water-in-oil type. Pastes comprised of absorptive powders dispersed in petroleum or hydrophilic petroleum containing the compound can also be suitable. A variety of occlusive devices can be used to release the compound into the blood stream, such as a semi-permeable membrane covering a reservoir containing the compound with or without a carrier, or a matrix containing the compound. Other occlusive devices are known in the literature.

Photodynamic compounds described herein can be administered rectally or vaginally in the form of a conventional suppository. Suppository formulations can be made from traditional materials, including cocoa butter, with or without the addition of waxes to alter the suppository's melting point, and glycerin. Water-soluble suppository bases, such as polyethylene glycols of various molecular weights, can also be used.

Lipid formulations or nanocapsules can be used to introduce photodynamic compound into host cells either in vitro or in vivo. Lipid formulations and nanocapsules can be prepared by methods known in the art.

To increase the effectiveness of the photodynamic compounds, it can be desirable to combine a compound with other agents effective in the treatment of the target disease or condition. For example, other active compounds (i.e., other active ingredients or agents) effective in treating the target disease can be administered with compounds of the present teachings. The other agents can be administered at the same time or at different times than the compounds disclosed herein.

Compounds of the present teachings can be useful for the treatment or inhibition of a pathological condition or disorder in a mammal, for example, a human subject. The present teachings accordingly provide methods of treating or inhibiting a pathological condition or disorder by providing to a mammal a compound of the present teachings including its pharmaceutically acceptable salt) or a pharmaceutical composition that includes one or more compounds of the present teachings in combination or association with pharmaceutically acceptable carriers. Compounds of the present teachings can be administered alone or in combination with other therapeutically effective compounds or therapies for the treatment or inhibition of the pathological condition or disorder.

Non-limiting examples of photodynamic compositions according to the present invention include from about 0.001 mg to about 1000 mg, or 0.01 mg to 250 mg, or 0.1 mg to 100 mg, or 1 to 25 mg of a photodynamic compound and one or more excipients.

The invention is useful for the treatment and diagnosis of disease states, particularly for the destruction of infectious organisms, hyperproliferating cells, and tumor cells. Preferred photodynamic compounds: (i) are metal-based coordination complexes; (ii) absorb and are activated by at least one of ultraviolet (UV) light, visible light, infrared (IR) light (particularly, near infrared (NIR) light) X-rays and gamma rays; (iii) kill human cancer cells in culture and in animals, and (iv) destroy bacteria and antibiotic-resistant bacteria.

Compositions of the invention are also capable of destroying microorganisms, such as *Staphylococcus aureus* (SA) and methicillin-resistant *S. aureus* (MRSA), with activation by at least one of UV light, visible light, IR light, NIR light, X-rays and gamma rays.

The invention will be illustrated in more detail with reference to the following Examples, but it should be understood that the present invention is not deemed to be limited thereto.

EXAMPLES

Example 1

It is established that visible and NIR light irradiation of Ru(II) and Os(II) based photosensitizers induces production of reactive oxygen species (ROS). Ru(II) photosensitizers have been proven to be stable under optical irradiation. Radiation stability of the photosensitizers under X-ray exposure was tested via visible light absorption (625 nm) after prior X-ray irradiation. This also revealed possible interactions between visible light and X-ray exposure on the photosensitizer's stability and ROS production.

The photosensitizers were diluted in water (2 mM stock concentration). The irradiation was performed in 96-well plates in 100 uL working volume at 500 μM working concentration of the photosensitizers in incomplete DMEM (not containing FBS and antibiotics). Generation of singlet oxygen was measured by fluorescence signal of SOG indicator (100 μM). The data are presented as the total fluorescence signal for increased exposure to visible (625 nm) light following X-ray exposure at different doses (5, 20 Gy). If not otherwise noted, the quantum energy of the X-rays was 225 keV.

The photosensitizers retained the ability to generate ROS, indicating their stability under X-ray exposure. Moreover, X-ray irradiation promoted significant augmentation of the generation of ROS, particularly of singlet oxygen as quantified using the singlet oxygen green (SOG) assay (FIG. 1). The time between X-ray exposure and the beginning of ROS measurement under visible light was less than 5 minutes. PDT is a quantum effect and it is expected that the rate of singlet oxygen production is a linear function of the number of X-ray photons interacting with the photosensitizer as demonstrated under visible light exposure without prior X-ray irradiation.

In contrast, generation of the singlet oxygen by visible light exposure is accelerated if the photosensitizers were previously exposed to X-rays. This acceleration following increasing photon absorption (equivalent to a photon dose dependent singlet oxygen yield) is certainly not an effect previously reported in literature.

FIGS. 1-4 show accelerated singlet oxygen generation by Ru(II) based TLD1433 (Ru(4,4'-dimethyl-2,2'-bipyridine)$_2$Cl$_2$), Os(II) based TLDOsH2B ([Os(biq)$_2$(LL)], (biq=2,2'-biquinoline and LL=1,10-phenanthroline), TLDOsH2IP ([Os(biq)$_2$(LL)] imidazo[4,5-f][1,10]phenanthroline) and TLDOsH$_2$dppn ([Os(biq)$_2$(LL)] benzo[i]dipyrido-[3,2-a:2', 3'-c]phenazine) (500 µM) during red light (625 nm) irradiation without or with prior exposure to X-ray irradiation (5 or 20 Gy).

The accelerated generation of singlet oxygen suggests that X-ray irradiation can change photochemical characteristics of Ru(II) and Os(II) based PSs facilitating ROS production upon red light irradiation, with the singlet oxygen quantum yield increasing with the increase of the number of absorbed photons. Ionizing radiation does not destroy the ability of photosensitizers to generate ROS, but predestine their chemical change upon further light activation.

In order to verify if this accelerated singlet oxygen generation is also translated into a biological system in terms of cell kill, the following in vitro experiments were performed.

Example 2

The capability of metal-based photosensitizers to exert a PDT effect upon irradiation by X-rays was assessed. X-ray activation of photosensitizers enables PDT on deep tumors impenetrable by visible light.

The cells were incubated in complete DMEM media containing antibiotics and 10% FBS (resulting in 2.5 µM bovine Tf in the medium) and all the solutions were prepared in this media. The cells were loaded with TLD1433 or TLDOsH2IP (20-80 µM) for 4 hours at 37° C. Subsequently, a wash with complete medium was performed followed by irradiation with red (625 nm, 90 J cm$^{-2}$) or near infrared (808 nm, 600 J cm$^{-2}$) light, X-ray (5 Gy, 225 keV), X-ray followed by light or light followed by X-ray. Matched dark controls were used in parallel: incubation at ambient conditions (ambient air, room temperature) for a length of time corresponding to the irradiation session. After irradiation, the cells were returned to the incubator. After 21 hours, the viability of cells was determined by Presto Blue assay, and cell kill was calculated as percent of matched control. Pure PDT effect was calculated in the following way: Pure PDT effect (percent cell kill)=Total PDT percent cell kill–Light alone percent cell kill–Dark percent cell kill.

X-ray irradiation (5 Gy, 225 KeV) with no photosensitizers resulted in no or very low cell kill (Tables 2, 6), as did the exposure to photosensitizers with no irradiation (Tables 1, 5). In contrast, an X-ray mediated PDT effect was achieved with both Ru(II)-based (TLD1433) and Os(II)-based (TLDOsH2IP) photosensitizers in HT1376 (a human bladder carcinoma) or U87 (a human primary glioblastoma) cells. The effect was more pronounced for Ru-based TLD1433 (Tables 2, 3, 6).

A sequential combination of X-ray and light irradiation showed a PDT effect greater than a sum of the separate effects of X-ray and PDT light (Tables 4, 7). The effect was thus synergistic, in contrast to an additive effect when the two separate effects are simply added together. This synergy could be more pronounced when X-ray irradiation was followed by light irradiation than with the reverse sequence of irradiations (Table 7).

As a result of the observed synergy, total PDT-induced cell kill could be increased achieving 2.3 logs (99.5%) cell kill of cancer cells that could not be obtained separately with light or X-rays (Table 8).

TABLE 1

Dark cell kill (%) induced in HT1376 cells by 20 µM TLD1433.

| Concentration | Dark |
| --- | --- |
| 20 uM | 0 |

TABLE 2

PDT cell kill (%) induced in HT1376 cells by 20 µM TLD1433 using red light (625 nm, 90 J cm$^{-2}$), X-ray irradiation (5 Gy, 225 KeV) and combined irradiation.

| Concentration | Red Light | X-ray | Red Light & X-ray |
| --- | --- | --- | --- |
| 0 uM | 0 | 0 | 0 |
| 20 uM | 9.9 | 33.4 | 93.2 |

TABLE 3

Pure PDT effect (% cell kill) induced in HT1376 cells by 20 µM TLD1433 using red light (625 nm, 90 J cm$^{-2}$), X-ray irradiation (5 Gy, 225 KeV) and combined irradiation.

| Concentration | Red Light | X-ray | Red Light & X-ray |
| --- | --- | --- | --- |
| 20 uM | 9.9 | 33.4 | 93.2 |

TABLE 4

Synergy in the pure PDT effect (% cell kill) induced in HT1376 cells by 20 µM TLD1433 using combined red light (625 nm, 90 J cm$^{-2}$) and X-ray irradiation (5 Gy, 225 KeV).

| Concentration | Red Light & X-ray |
| --- | --- |
| 20 uM | 49.9 |

TABLE 5

Dark cell kill (%) induced in U87 cells by 20 µM OsH2IP.

| Concentration | Dark |
| --- | --- |
| 20 uM | 5.1 |

TABLE 6

PDT cell kill (%) and pure PDT effect (% cell kill, in brackets) induced in U87 cells by 20 µM OsH2IP using near infrared light (808 nm, 600 J cm$^{-2}$), X-ray irradiation (5 Gy, 225 KeV) and combined irradiation.

| Concentration | Near Infrared | X-ray | X-ray & Near Infrared | Near Infrared & X-ray |
| --- | --- | --- | --- | --- |
| 0 uM | 0 | 1.9 | 5.2 | 9.3 |
| 20 uM | 24.6 (19.5) | 13.8 (6.8) | 50.0 (39.6) | 31.5 (17.0) |

TABLE 7

Synergy in the pure PDT effect (% cell kill) induced in U87 cells by 20 μM OsH2IP using combined near infrared light (808 nm, 600 J cm−2) and X-ray irradiation (5 Gy, 225 KeV).

| Concentration | X-ray & Near Infrared | Near Infrared & X-ray |
|---|---|---|
| 20 uM | 13.4 | −9.3 |

TABLE 8

Dark cell kill (%), PDT cell kill (%) and pure PDT effect (% cell kill, in brackets) induced in HT1376 cells by 80 μM TLD1433 using near infrared light (808 nm, 600 J cm$^{-2}$), X-ray irradiation (5 Gy, 225 KeV) and combined irradiation.

| Concentration | Dark | Near Infrared | X-ray | X-ray & Near Infrared | Near Infrared & X-ray |
|---|---|---|---|---|---|
| 0 uM | 0.0 | 24.6 | 28.3 | 40.7 | 46.3 |
| 80 uM | 2.3 | 45.9 (19.0) | 66.4 (35.8) | 99.5 (56.5) | 71.3 (22.7) |

Example 3

Premixing of the photosensitizers with transferrin (Tf) improves their selective uptake into tumor cells and potentially improves X-ray mediated PDT effect. Ruthenium based TLD1433 (80 μM) and human apo-Tf (5 μM) were used to assess the effect of Tf on visible light or X-ray mediated PDT effect on U87 (human glioblastoma) and HT1376 (human urinary bladder carcinoma) cell cultures.

The cells were incubated in incomplete DMEM media containing antibiotics but not FBS (to control for Tf presence), and all the solutions were prepared in this media.

A photosensitizer (TLD1433) was pre-mixed with human Tf, to achieve 80 μM TLD1433 and 5 μM Tf and incubated for 30 minutes at room temperature. In the control group, an equivalent volume of incomplete medium (no photosensitizer, no Tf) was added.

The cells were loaded with TLD1433 in incomplete medium or with TLD1433-Tf premix. Incomplete medium alone and medium with Tf were used as matched controls. Loading time was 2 hours at 37° C., followed by subsequent wash with incomplete medium and irradiation with red light (625 nm, 90 J Improving effect of transferrin), X-ray (5 Gy, 225 keV), X-ray followed by red light or red light followed by X-ray. Matched dark controls ("Dark R" and "Dark X") were used in parallel. The Dark R control was incubated at ambient conditions (ambient air, room temperature) for a time length corresponding to that of the red light irradiation test. The Dark X control was incubated at ambient conditions (ambient air, room temperature) for a time length corresponding to that of the X-ray irradiation test. After irradiation, the medium was changed with complete DMEM (containing FBS), and the cells were returned to incubator. After 21 hours, the viability of cells was determined by Presto Blue assay, and cell kill was calculated as percent of matched control (no drug, no light, no Tf).

As shown in Table 9, the presence of Tf decreased dark toxicity (photosensitizer alone) of Ru(II)-based TLD1433 and increased PDT effect under X-ray irradiation on U87 and HT1376 cancer cell lines.

TABLE 9

Effect of 5 μM Tf on 80 μM TLD1433 dark toxicity (% cell kill) and TLD1433-mediated pure PDT effect (% cell kill) using X-ray irradiation (5 Gy, 225 kEv).

| | | Cell Kill (%) | |
|---|---|---|---|
| Cells | X-ray Irradiation | No Tf | 5 μM Tf |
| U87 | None (Dark toxicity) | 57.5 | 43.7 |
| U87 | 5 Gy (Pure PDT Effect) | 42.5 | 56.3 |
| HT1376 | None (Dark toxicity) | 59.3 | 40.7 |
| HT1376 | 5 Gy (Pure PDT Effect) | 40.0 | 58.6 |

Tf decreases dark toxicity of the photosensitizers. This contributes to an increased safety of PDT treatment in the presence of Tf. Also, in the presence of Tf, PDT efficacy of TLD1433 under ionizing (X-ray) irradiation is increased. This finding is similar to the previously observed effect of Tf on PDT under non-ionizing (visual light) irradiation.

Example 4

Ru(II)-based TLD1433 (80 μM) and human apo-Tf (5 μM) were used to assess the effect of Tf on visible light or X-ray mediated PDT effect on U87 (human glioblastoma) and HT1376 (human urinary bladder carcinoma) cell cultures.

The cells were incubated in incomplete DMEM media containing antibiotics but not FBS (to control for Tf presence), and all the solutions were prepared in this media.

A photosensitizer (TLD1433) was pre-mixed with human Tf, to achieve 80 μM TLD1433 and 5 μM Tf and incubated for 30 minutes at room temperature. In the control group, an equivalent volume of incomplete medium (no photosensitizer, no Tf) was added.

The cells were loaded with TLD1433 in incomplete medium or with TLD1433-Tf premix. Incomplete medium alone and medium with Tf were used as matched controls. Loading time was 2 hours at 37° C., followed by subsequent wash with incomplete medium and irradiation with red light (625 nm, 90 J Improving effect of transferrin), X-ray (5 Gy, 225 keV), X-ray followed by red light or red light followed by X-ray. Matched dark controls ("Dark R" and "Dark X") were used in parallel. The Dark R control was incubated at ambient conditions (ambient air, room temperature) for a time length corresponding to that of the red light irradiation test. The Dark X control was incubated at ambient conditions (ambient air, room temperature) for a time length corresponding to that of the X-ray irradiation test. After irradiation, the medium was changed with complete DMEM (containing 10% FBS), and the cells were returned to incubator. After 21 hours, the viability of cells was determined by Presto Blue assay, and cell kill was calculated as percent of matched control (no drug, no light, no Tf). Pure PDT effect was calculated in the following way: Pure PDT effect (percent cell kill)=Total PDT percent cell kill−Irradiation alone percent cell kill−Dark percent cell kill.

As shown in Table 10, Tf increased TLD1433 PDT efficacy under a combination of red light and X-ray irradiation. Under red light followed by X-ray, % cell kill was increased from 28.7 to 42.5 for U87 cells and from 0 to 16.5 for HT1376 cells. Under X-ray (5 Gy) followed by red light (625 nm, 90 J cm$^{-2}$) irradiation, the increase in % cell kill was from 16.9 to 45.1 for U87 cells and from 29.4 to 48.0 for HT1376 cells.

TABLE 10

Facilitating effect of Tf (5 μM) on pure PDT effect (% cell kill) by TLD1433 (80 μM) using X-rays (5 Gy, 225 keV) and red light (625 nm, 90 J Improving effect of transferrin).

| Cells | Tf (μM) | Pure PDT Effect | |
|---|---|---|---|
| | | Red Light & X-ray | X-ray & Red Light |
| U87 | 0 | 28.7 | 16.9 |
| U87 | 5 | 42.5 | 45.1 |
| HT1376 | 0 | 0 | 29.4 |
| HT1376 | 5 | 16.5 | 48.0 |

Example 5 (Prophetic)

A mixed metal Ru(II)-Rh(II)-based photosensitizer TLD7 (20 μM) is tested. Due to their inherent polarity, heterobimetallic photosensitizers are able to the charge transfer across the molecule as PDT effector.

The structural formula of TLD7 is:

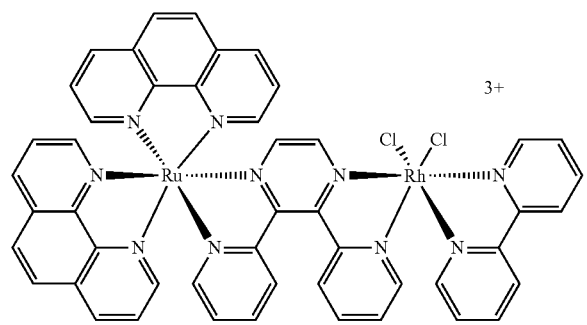

with the following properties:
MEC at 525 nm=14042 M-1 cm-1
MEC at 625 nm=1527 M-1 cm-1
MEC at 800 nm=168 M-1 cm-1
MW=1131.5 g/mol.

Effects of TLD7 mediated PDT using red light or X-ray are tested on U87 (human glioblastoma) cell culture. The cells are incubated in complete DMEM media containing antibiotics and 10% FBS (resulting in 2.5 μM bovine Tf in the medium), and all the solutions are prepared in this media. The cells are loaded with 20 μM TLD7 for 4 hours at 37° C. Subsequently, the cells are washed with complete medium and irradiated with red light (625 nm, 90 J Improving effect of transferrin), X-ray (5 Gy, 225 keV), X-ray followed by red light or red light followed by X-ray. Matched dark controls are used in parallel: incubation at ambient conditions (ambient air, room temperature). After irradiation, the cells are returned to incubator. After 21 hours, the viability of cells is determined by Presto Blue assay, and cell kill is calculated as percent of matched control (no drug, no light). Pure PDT effect is calculated in the following way: Pure PDT effect (percent cell kill)=Total PDT percent cell kill–Light alone percent cell kill–Dark percent cell kill.

TLD7 will demonstrate low dark toxicity (Table 11) and also show PDT activity not only in red light but also after X-ray irradiation (Table 12). X-ray irradiation followed by red light PDT (but not the opposite order of treatments) induced synergistic increase in PDT cell kill (Table 13). The data suggest that TLD7 has potential of cell kill under X-ray irradiation, and this capability is facilitated in combination with red light PDT.

TABLE 11

(Prophetic). Dark toxicity (% cell kill) by TLD7 (20 μM) in U87.

| Concentration | Dark |
|---|---|
| 20 uM | 5.1 |

TABLE 12

(Prophetic). Pure PDT effect (% cell kill) by TLD7 (20 μM) using red light (625 nm, 90 J Improving effect of transferrin), X-ray irradiation (5 Gy, 225 keV) and combined irradiation in U87 cells.

| Concentration | Red | X-ray | X-ray & Red | Red & X-ray |
|---|---|---|---|---|
| 20 uM | 19.5 | 6.8 | 39.6 | 17.0 |

TABLE 13

(Prophetic). Synergy in the pure PDT effect (% cell kill) by TLD7 (20 μM) using combined red light (625 nm, 90 J Improving effect of transferrin) and X-ray irradiation (5 Gy, 225 keV) in U87 cells.

| Concentration | X-ray & Red | Red & X-ray |
|---|---|---|
| 20 uM | 13.4 | −9.3 |

Example 6 (Prophetic)

Ru(II)-Ru(II)-based homobimetallic photosensitizer TLD002 (20 μM) are tested. Homobimetallic photosensitizers are able to energy transfer as the dominant PDT effector.

Effects of TLD002 mediated PDT by red light or X-ray are tested on U87 (human glioblastoma) cell culture. The cells are incubated in complete DMEM media containing antibiotics and 10% FBS (resulting in 2.5 uM bovine Tf in the medium), and all the solutions are prepared in this media. The cells are loaded with TLD002 for 4 hours at 37° C. Subsequently, the cells are washed with complete medium and irradiated with red light (625 nm, 90 J cm$^{-2}$), X-ray (5 Gy, 225 keV), X-ray followed by red light or red light followed by X-ray. Matched dark controls are used in parallel: incubation at ambient conditions (ambient air, room temperature). After irradiation, the cells are returned to the incubator. After 21 hours, the viability of cells is determined by Presto Blue assay, and cell kill is calculated as percent of matched control (no drug, no light). Pure PDT effect is calculated in the following way: Pure PDT effect (percent cell kill)=Total PDT percent cell kill–Light alone percent cell kill–Dark percent cell kill.

TLD002 demonstrates low dark toxicity (Table 14) and shows PDT activity not only in red light but also after X-ray irradiation (Table 15). X-ray irradiation followed by red PDT (but not the opposite order of treatments) induces a synergistic increase in PDT cell kill (Table 16). The data suggest that TLD002 has potential of cell kill under X-ray irradiation, and this capability is facilitated in combination with red light PDT.

TABLE 14

(Prophetic). Dark toxicity (% cell kill) by TLD002 (20 μM) in U87 cells.

| Concentration | Dark |
|---|---|
| 20 uM | 2.8 |

TABLE 15

(Prophetic). Pure PDT effect (% cell kill) by TLD002 (20 μM) using red light (625 nm, 90 J Improving effect of transferrin), X-ray irradiation (5 Gy, 225 keV) and combined irradiation in U87 cells.

| Concentration | Red | X-ray | X-ray & Red | Red & X-ray |
|---|---|---|---|---|
| 20 uM | 24.6 | 20.0 | 71.7 | 53.4 |

TABLE 16

(Prophetic). Synergy in the pure PDT effect (% cell kill) by TLD002 (20 μM) using combined red (625 nm, 90 J Improving effect of transferrin), X-ray irradiation (5 Gy, 225 keV) in U87 cells.

| Concentration | X-ray & Red | Red & X-ray |
|---|---|---|
| 20 uM | 27.1 | 8.8 |

Example 7

Transition metals-based PSs can absorb in the X-ray range. This can be used in diagnostics during PDT considering selective uptake of these PSs by malignant tumors.

Testing for novel delivery vehicles for these drugs by CT imaging is feasible. Longitudinal pharmacokinetic studies of transition metal-based PS are also possible in individual animals for times comparable to maximum permissible times under anesthesia.

Moreover, it is valuable as an input parameter for the treatment planning software as is shown in high resolution images of one of the PDT efficacy determining parameters.

For in vivo imaging of the photosensitizer, a rat was injected with 1 mg/kg of OsH2dppn via tail vein and imaged with a small animal CT scanner as a function of time post-systemic administration (5, 10, 30 min, 1, 2, 4 hours).

OsH2dppn can be detected on CT images at 1 mg/kg concentration presumably accumulating in the bladder over time. See FIGS. 5A-5E, wherein a circle is drawn over each image to highlight the location of the OsH2dppn. Please note that these images represent only direct reconstruction. Visualization of the PS can be further improved when differential images to the pre-injection background are calculated.

Ru(II) and Os(II) complexes based photosensitizers enable ionizing radiation based detection in vivo. This opens the ability for 3D photosensitizer distribution quantification to be used for improvement in PDT dosimetry when convoluted with the local fluence rate. 3D reconstructions can be performed by, e.g., using the imaging program MIPAV.

Example 8

CT26.WT (murine adenocarcinoma cells) tumors were induced subcutaneously in Balb/C mice. A premix of Ruthenium (TLD1433) based photosensitizer and Optiferrin® at a TLD1433:OPTIFERRIN molar ratio of 79 was dissolved in saline with 20% propylenglycol (PG) and injected intratumorally at a dose of 10 mg TLD1433 per kg body weight (BW) in a volume of 100 uL per each 20 g BW. Following 4 hours, the tumor was irradiated with X-ray (1 Gy, 225 keV). The formalin fixed, paraffin embedded tissues were sectioned, H&E stained and the sections imaged under 40× magnification.

Figure 6A:
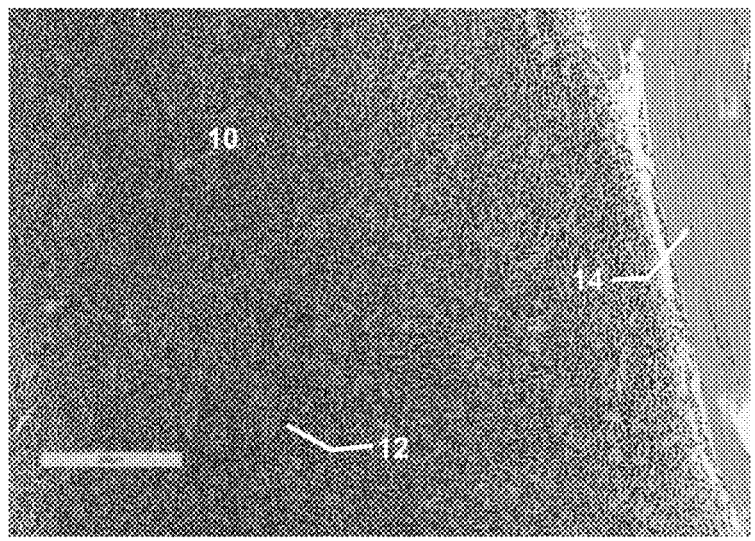
FIGS. 6A, 6B and 6C show images of stained tissue sections at 40× magnification.
Figure 6B:
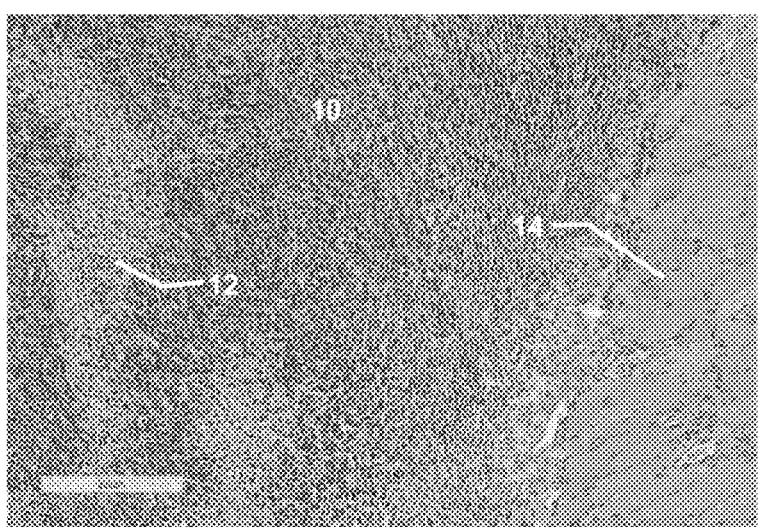
Figure 6C:
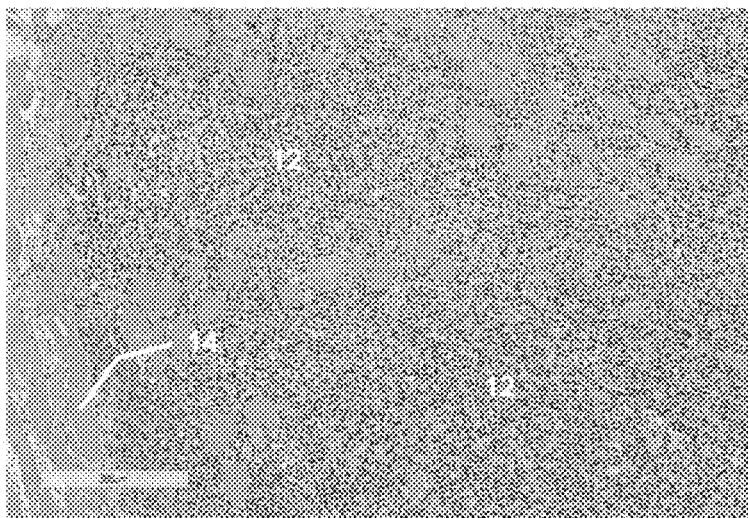

FIG. 6A shows untreated tumor, FIG. 6B shows a tumor irradiated with X-ray alone and FIG. 6C shows the effect of X-ray irradiation in the presence of TLD1433 and OPTIFERRIN premix. The cells in the untreated tumor 10 are characterized by relatively large nuclei and prevalence of nucleophilic (blue—shown as dark gray in grayscale) stain. There are only small isolated pockets of necrosis 12 characterized by shrunk dark nuclei and predominantly eosinophilic (pink—shown as light gray in grayscale) stain of the area. X-ray alone tumor demonstrates only limited necrosis with the tumor largely not damaged. Importantly, no damage is observed in the underlying muscle 14 suggesting safety of 1Gy X-ray irradiation for normal tissues. In the presence of TLD1433 & OPTIFERRIN premix, X-ray irradiation induces massive necrosis 12 in tumor with no damage to the underlying muscle 14. The latter also suggests selective intratumoral location of the photosensitizer with no uptake by the underlying muscle 14.

While the invention has been described in detail and with reference to specific examples thereof, it will be apparent to one skilled in the art that various changes and modifications can be made therein without departing from the spirit and scope thereof.

What is claimed is:

1. A method for destroying cells and/or microorganisms in an organism, said method comprising:
   administering to the organism a composition comprising a photodynamic compound which is a metallosupramolecular complex containing at least one transition metal selected from the group consisting of osmium, manganese, molybdenum, rhenium, ruthenium, iron, cobalt, rhodium, iridium, nickel, platinum, and copper; and
   irradiating the photodynamic compound in the organism with electromagnetic radiation,
   wherein the electromagnetic radiation comprises X-ray radiation and non-ionizing radiation administered in an order and at a power which are synergistically effective to: (a) inhibit proliferation of hyperproliferating cells in the organism and/or (b) destroy microorganisms in the organism.

2. The method of claim 1, wherein the microorganisms are at least one member selected from the group consisting of bacteria, viruses and fungi.

3. The method of claim 1, wherein the organism is a human.

4. The method of claim 1, wherein the composition is administered by topical, oral, buccal, intravenous, intramuscular, intra-arterial, intramedullary, intrathecal, intraventricular, transdermal, subcutaneous, intraperitoneal, intranasal, enteral, topical, sublingual, vaginal, ophthalmic, pulmonary or rectal routes.

5. The method of claim 1, wherein the composition is pharmaceutically acceptable and further comprises at least one pharmaceutically acceptable carrier, excipient or diluent.

6. The method of claim 1, wherein the composition further comprises a metal-binding glycoprotein.

7. The method of claim 6, wherein the metal-binding glycoprotein is transferrin.

8. The method of claim 1, wherein the non-ionizing radiation is in a range from 600-950 nm.

9. The method of claim 1, wherein the irradiating step comprises irradiating the organism with 0.1 to 100 Gy of the X-ray radiation and with the non-ionizing radiation in a range from 600-950 nm.

10. The method of claim 1, which is conducted without a molecular conjugate comprising a radioluminescent molecule and a photosensitizer.

11. The method of claim 1, wherein the photodynamic compound has the formula (I):

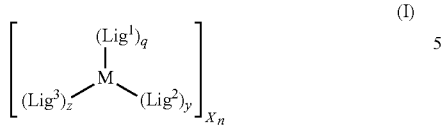

including hydrates, solvates, pharmaceutically acceptable salts, prodrugs and complexes thereof, wherein:

M at each occurrence is independently selected from the group consisting of osmium, ruthenium and rhodium;

X is selected from the group consisting of $Cl^-$, $PF_6^-$, $Br^-$, $BF_4^-$, $ClO_4^-$, $CF_3SO_3^-$, and $SO_4^{-2}$;

n=0, 1, 2, 3, 4, or 5;

q is independently at each occurrence 0, 1, or 2;

y is independently at each occurrence 0, 1, or 2;

z is independently at each occurrence 1, 2, or 3;

$Lig^1$ is a bidentate ligand that at each occurrence is each independently selected from the group consisting of

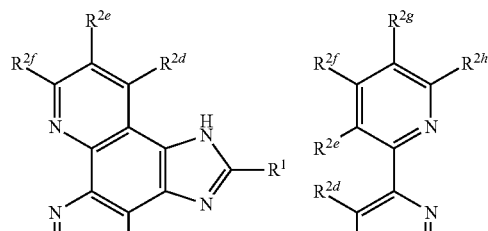

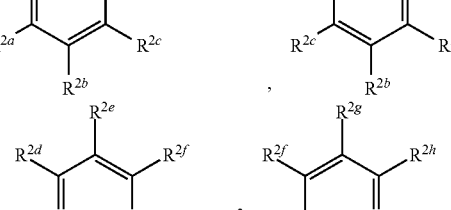

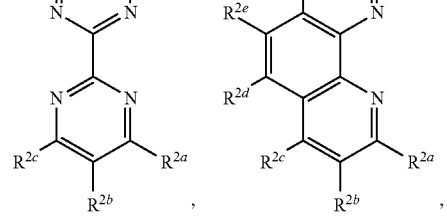

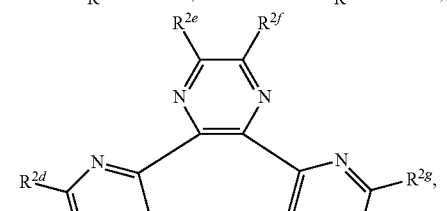

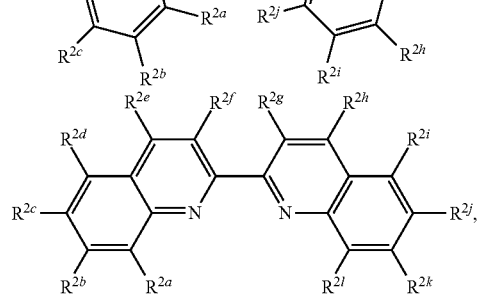

-continued

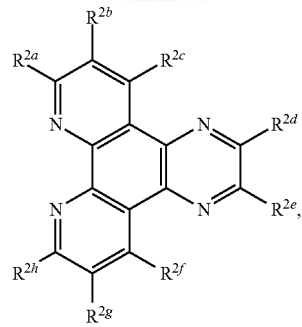

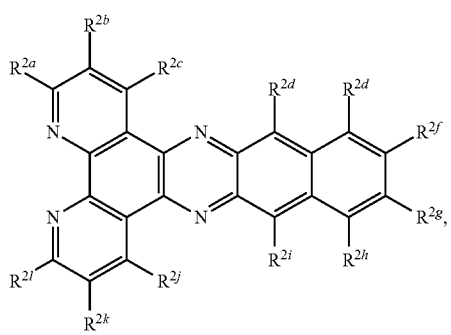

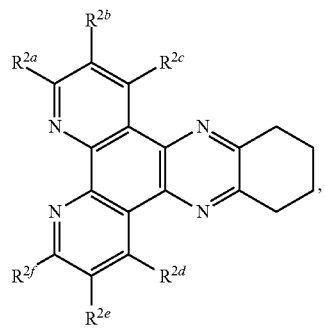

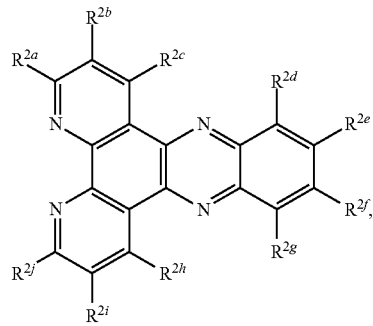

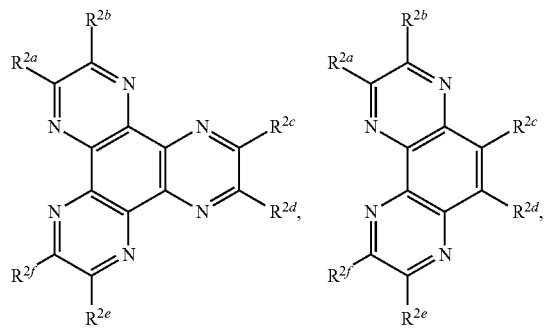

-continued
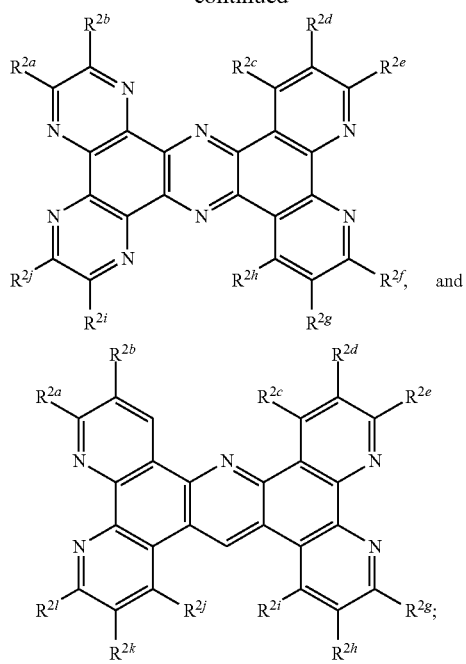
and
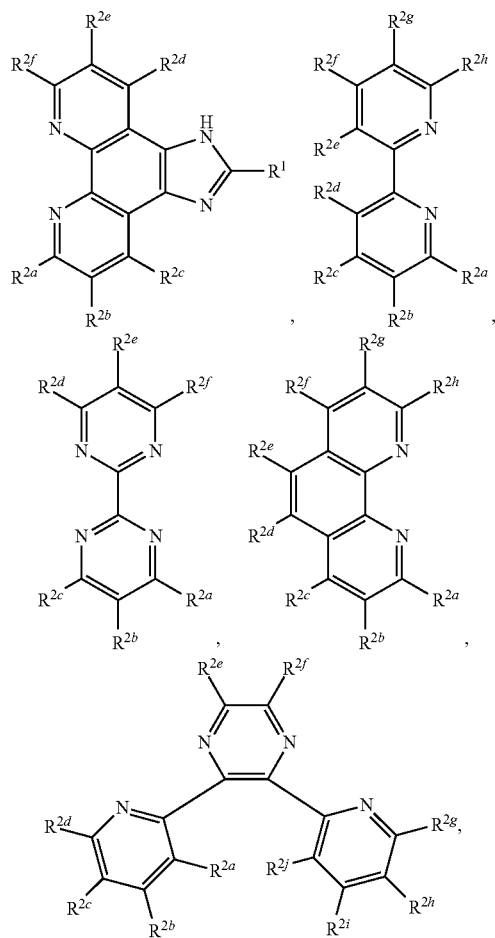
Lig² is a bidentate ligand that at each occurrence is each independently selected from the group consisting of
-continued
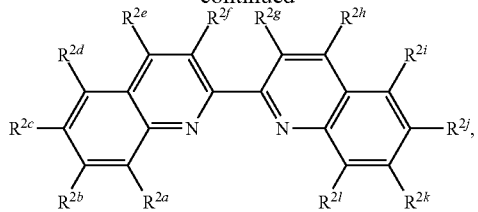
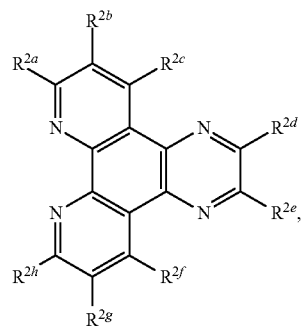
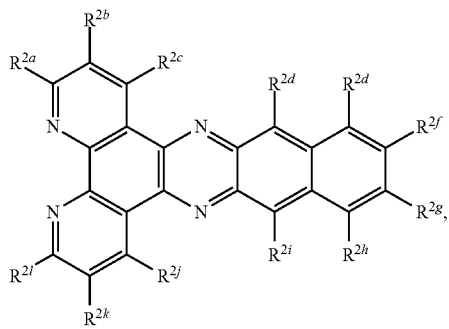
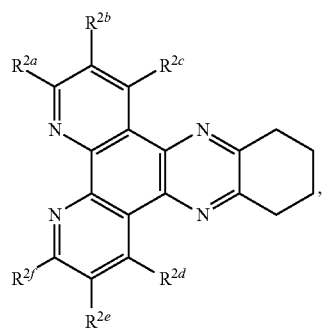
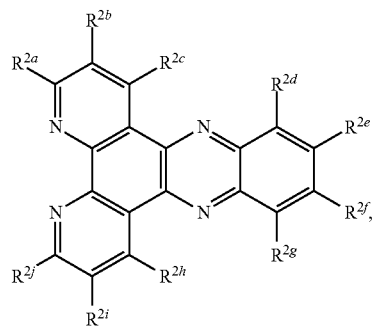

-continued
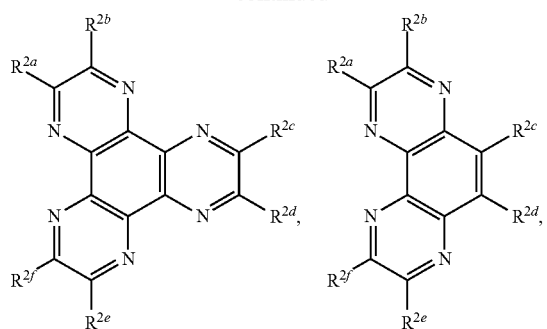
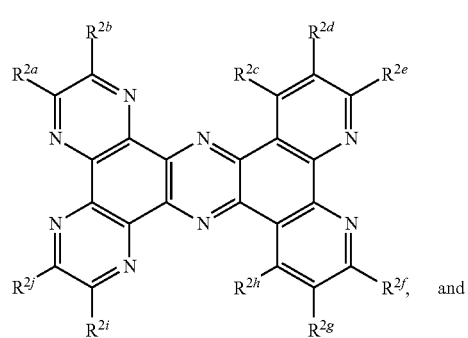
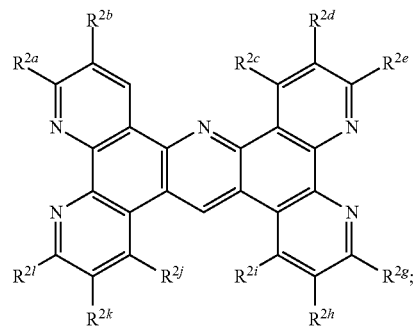
Lig³ is a bidentate ligand that at each occurrence is each independently selected from the group consisting of
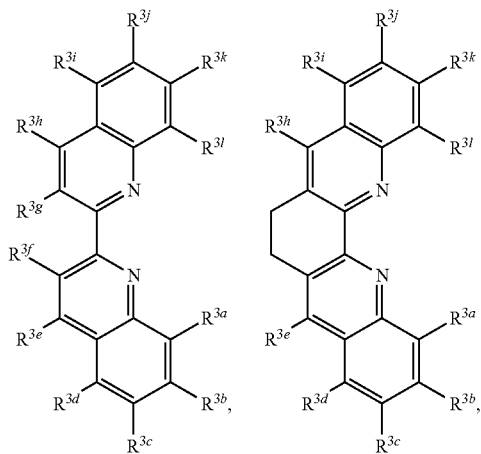
-continued
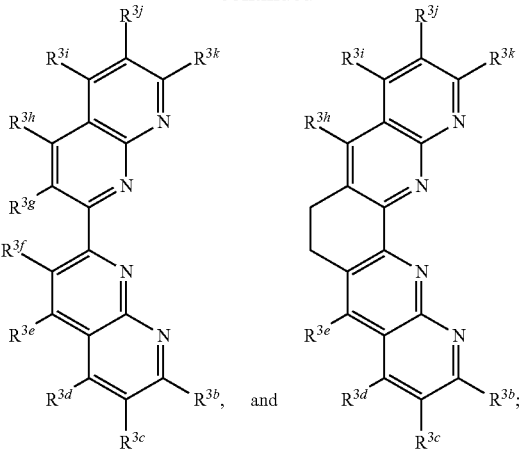
R¹ is selected from the group consisting of hydrogen, optionally substituted phenyl, optionally substituted aryl, optionally substituted heteroaryl, 4-pyridyl, 3-pyridyl, 2-thiazole, 2-pyrolyl, 2-furanyl,
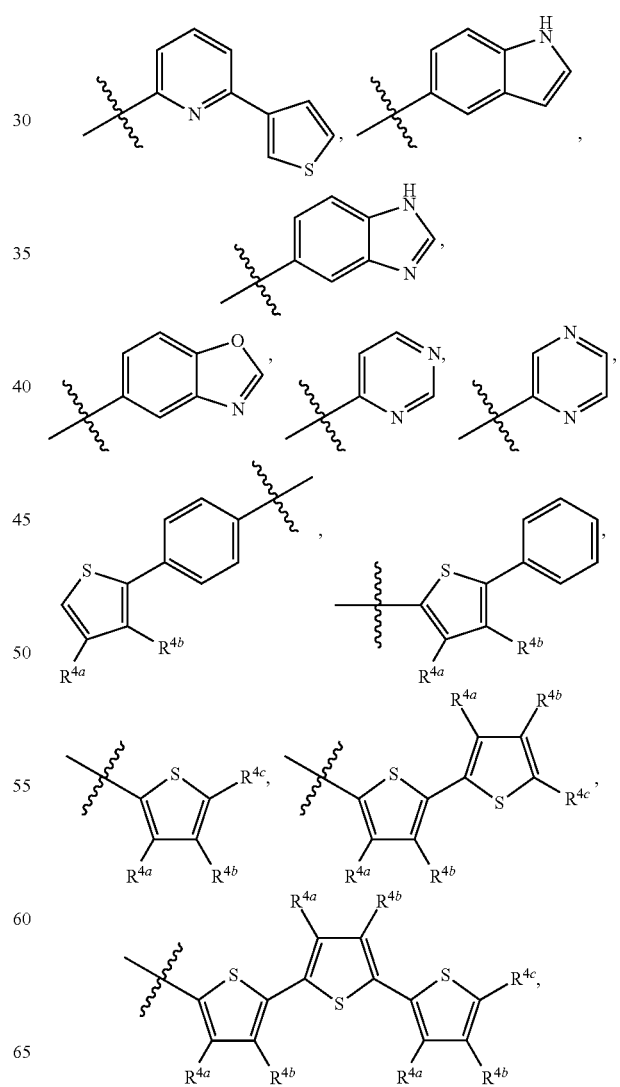

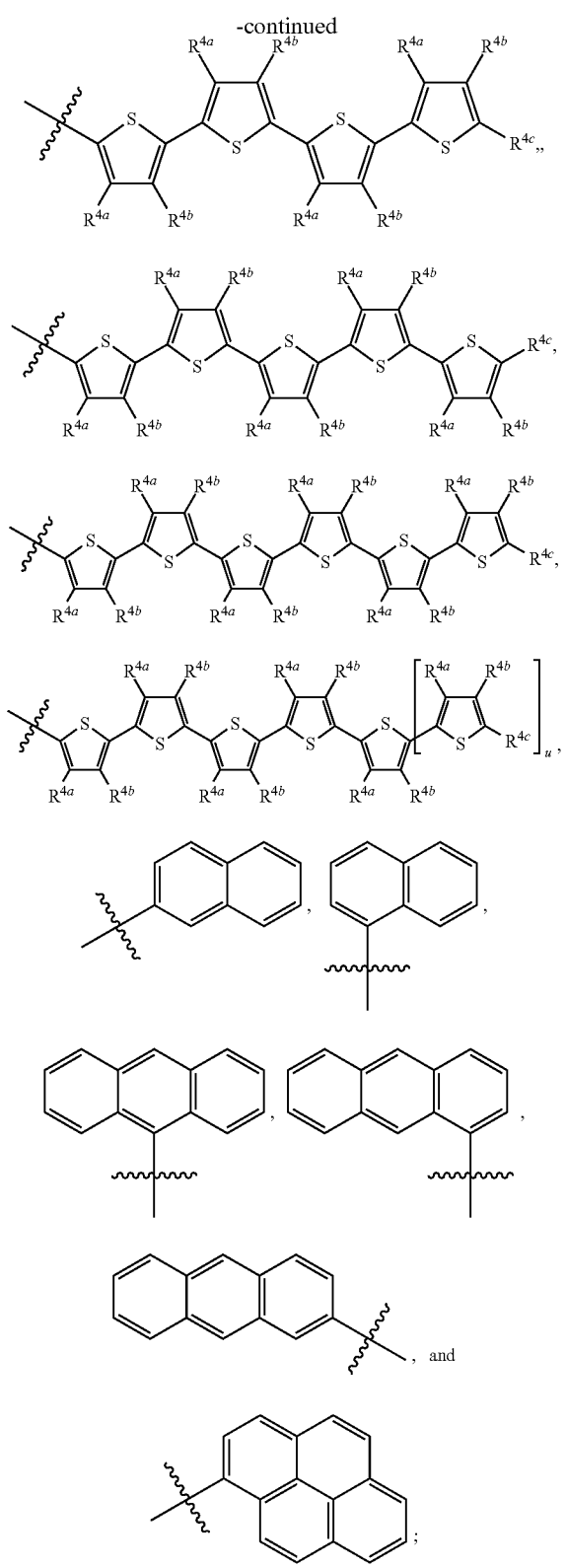

u is an integer;
R$^{2a}$, R$^{2b}$, R$^{2c}$, R$^{2d}$, R$^{2e}$, R$^{2f}$, R$^{2g}$, R$^{2h}$, R$^{2i}$, R$^{2j}$, R$^{2k}$, and R$^{2l}$ at each occurrence are each independently selected from the group consisting of hydrogen, C$_{1-6}$ optionally substituted alkyl, C$_{1-6}$ optionally substituted branched alkyl, C$_{3-7}$ optionally substituted cycloalkyl, C$_{1-6}$ optionally substituted haloalkyl, C$_{1-6}$ optionally substituted alkoxy, CO$_2$R$^5$, CONR$^6_2$, NR$^7_2$, SO$_3$H, sulfate, sulfonate, optionally substituted aryl, optionally substituted aryloxy, optionally substituted heteroaryl, and optionally substituted heterocycle;

R$^{3a}$, R$^{3b}$, R$^{3c}$, R$^{3d}$, R$^{3e}$, R$^{3f}$, R$^{3g}$, R$^{3h}$ R$^{3i}$, R$^{3j}$, R$^{3k}$, and R$^{3l}$ at each occurrence are each independently selected from the group consisting of hydrogen, C$_{1-6}$ optionally substituted alkyl, C$_{1-6}$ optionally substituted branched alkyl, C$_{1-6}$ optionally substituted haloalkyl, C$_{1-6}$ optionally substituted alkoxy, optionally substituted phenyl, and CO$_2$R$^8$;

R$^{4a}$, R$^{4b}$, and R$^{4c}$ at each occurrence are each independently selected from the group consisting of hydrogen, C$_{1-6}$ optionally substituted alkyl, C$_{1-6}$ optionally substituted branched alkyl, C$_{1-6}$ optionally substituted cycloalkyl, C$_{1-6}$ optionally substituted haloalkyl, C$_{1-6}$ optionally substituted alkoxy, CO$_2$R$^5$, CONR$^6_2$, NR$^7_2$, sulfate, sulfonate, optionally substituted aryl, optionally substituted aryloxy, optionally substituted heteroaryl, and optionally substituted heterocycle;

R$^{4a}$ and R$^{4b}$ at each occurrence on a thiophene ring are taken together with the atom to which they are bound to form an optionally substituted ring having from 6 ring atoms containing 2 oxygen atoms;

R$^5$ at each occurrence are each independently selected from the group consisting of hydrogen and optionally substituted alkyl;

R$^6$ at each occurrence are each independently selected from the group consisting of hydrogen and optionally substituted alkyl;

R$^7$ at each occurrence are each independently selected from the group consisting of hydrogen and optionally substituted alkyl; and R$^8$ at each occurrence are each independently selected from the group consisting of hydrogen and optionally substituted alkyl.

12. The method of claim 1, wherein the photodynamic compound has a structure selected from the group consisting of:

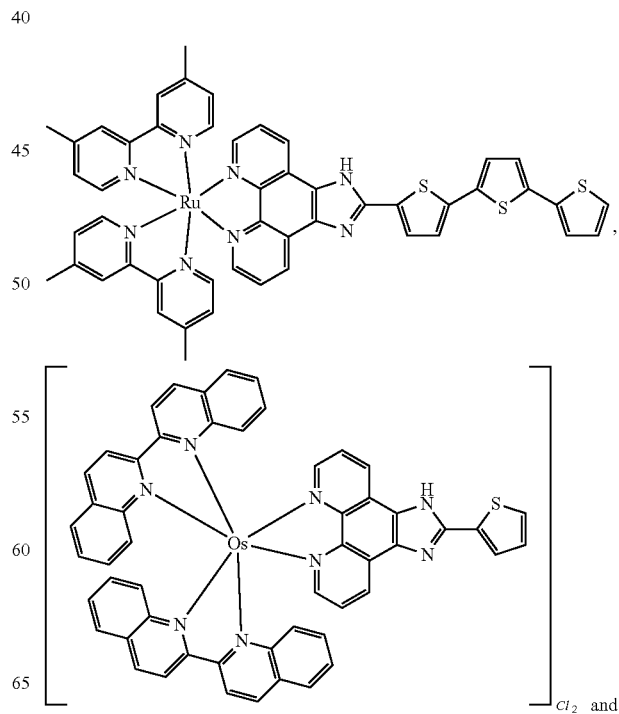

-continued

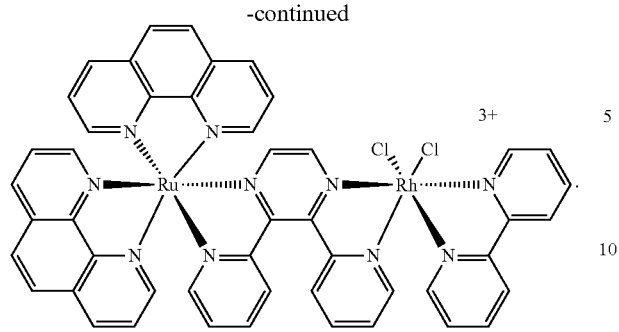

13. A method for destroying cells and/or microorganisms in an organism, said method comprising:
   administering to the organism a composition comprising a photodynamic compound which is a metallosupramolecular complex containing at least one transition metal selected from the group consisting of osmium, manganese, molybdenum, rhenium, ruthenium, iron, cobalt, rhodium, iridium, nickel, platinum, and copper; and
   irradiating the photodynamic compound in the organism with gamma rays and non-ionizing radiation effective to activate the photodynamic compound to destroy at least one of the cells and the microorganisms in the organism.

* * * * *